(12) United States Patent
Somei et al.

(10) Patent No.: US 11,448,245 B2
(45) Date of Patent: Sep. 20, 2022

(54) WALL ATTACHMENT SYSTEM

(71) Applicant: KALTECH CORPORATION, Osaka (JP)

(72) Inventors: Junichi Somei, Osaka (JP); Kenji Hatazawa, Osaka (JP); Toyohiro Harazono, Osaka (JP); Hirohiko Ueda, Osaka (JP)

(73) Assignee: KALTECH CORPORATION, Osaka (JP)

( * ) Notice: Subject to any disclaimer, the term of this patent is extended or adjusted under 35 U.S.C. 154(b) by 0 days.

(21) Appl. No.: 16/997,546

(22) Filed: Aug. 19, 2020

(65) Prior Publication Data

US 2021/0180624 A1 Jun. 17, 2021

(30) Foreign Application Priority Data

Dec. 13, 2019 (JP) .............................. JP2019-225227

(51) Int. Cl.
| | |
|---|---|
| *F16B 1/00* | (2006.01) |
| *A61L 9/18* | (2006.01) |
| *A23L 3/3409* | (2006.01) |
| *B01D 53/86* | (2006.01) |
| *B01D 53/88* | (2006.01) |

(52) U.S. Cl.
CPC .................. *F16B 1/00* (2013.01); *A61L 9/18* (2013.01); *A23L 3/3409* (2013.01); *A23V 2002/00* (2013.01); *A61L 2209/15* (2013.01); *B01D 53/864* (2013.01); *B01D 53/885* (2013.01); *B01D 2255/802* (2013.01); *B01D 2257/7022* (2013.01); *B01D 2257/90* (2013.01); *B01D 2257/91* (2013.01); *F16B 2001/0035* (2013.01)

(58) Field of Classification Search
CPC combination set(s) only.
See application file for complete search history.

(56) References Cited

U.S. PATENT DOCUMENTS

| | | | | | |
|---|---|---|---|---|---|
| 3,827,020 | A | * | 7/1974 | Okamoto | .................. H01F 7/02 |
| | | | | | 335/285 |
| 4,211,382 | A | * | 7/1980 | Bonfils | .................. A47G 1/168 |
| | | | | | 248/467 |
| 4,605,292 | A | * | 8/1986 | McIntosh | ................. A47G 1/00 |
| | | | | | 248/205.3 |
| 4,852,284 | A | * | 8/1989 | Faggiano | .................. G09F 7/00 |
| | | | | | 40/488 |

(Continued)

FOREIGN PATENT DOCUMENTS

| | | |
|---|---|---|
| EP | 2100626 | 9/2009 |
| JP | S57-087208 U | 5/1982 |

(Continued)

*Primary Examiner* — Monica E Millner
(74) *Attorney, Agent, or Firm* — Hamre, Schumann, Mueller & Larson, P.C.

(57) ABSTRACT

A wall attachment system is provided that includes an object to be mounted, and an attachment unit for attaching the object to be mounted to a wall surface. The object to be mounted has a back surface installed with a metal. The attachment unit has a front surface installed with a magnet. The wall attachment system is configured so that the metal and the magnet contact each other in response to the object to be mounted being set in position for installation on the attachment unit.

13 Claims, 29 Drawing Sheets

(56) References Cited

U.S. PATENT DOCUMENTS

| | | | |
|---|---|---|---|
| 4,875,654 A * | 10/1989 | Chandonnet | A47G 1/17 248/467 |
| 5,269,083 A * | 12/1993 | Vampatella | A47G 1/065 248/206.5 |
| 5,400,479 A * | 3/1995 | Medina | H01F 7/0263 24/303 |
| D392,379 S | 3/1998 | Nash et al. | |
| D394,100 S | 5/1998 | Promseeda | |
| 6,405,983 B1 * | 6/2002 | Goj | F16B 19/1081 248/205.1 |
| D544,081 S | 6/2007 | Fujii | |
| D605,272 S | 12/2009 | Chun et al. | |
| D645,130 S | 9/2011 | Goldstein et al. | |
| 8,042,308 B2 * | 10/2011 | Sullivan | G09F 19/22 52/238.1 |
| 8,434,730 B2 * | 5/2013 | Ahlstrom | A47G 1/168 248/467 |
| 9,328,754 B2 * | 5/2016 | Stokes | F16B 5/0692 |
| 9,374,927 B2 * | 6/2016 | Byeon | G02F 1/133308 |
| D762,290 S | 7/2016 | Jepson et al. | |
| 9,642,480 B1 * | 5/2017 | Tanger | A47G 1/17 |
| 10,139,720 B2 * | 11/2018 | Yu | F16M 11/046 |
| D840,012 S | 2/2019 | Zhou | |
| 10,237,384 B2 * | 3/2019 | Holder | B60R 11/0241 |
| D873,398 S | 1/2020 | Seo | |
| 10,663,106 B1 * | 5/2020 | Meskan | F16M 11/18 |
| D916,264 S | 4/2021 | Jun | |
| 11,116,863 B2 | 9/2021 | Kim et al. | |
| 2009/0229967 A1 | 9/2009 | Sakatani | |
| 2011/0042542 A1 * | 2/2011 | Russo | A47G 1/17 248/467 |
| 2012/0280098 A1 * | 11/2012 | Rinck | F21S 4/10 248/304 |
| 2013/0052090 A1 | 2/2013 | Bohlen | |
| 2013/0149504 A1 * | 6/2013 | Reingewirtz | H01F 7/0215 428/179 |
| 2013/0229802 A1 * | 9/2013 | Fukushima | F21V 23/06 362/235 |
| 2014/0061409 A1 * | 3/2014 | Mayhew, Jr. | F16M 13/02 248/206.5 |
| 2014/0263908 A1 * | 9/2014 | Franklin | F16M 11/14 248/309.4 |
| 2016/0003270 A1 * | 1/2016 | Franklin | H01F 7/0221 439/529 |
| 2016/0033194 A1 * | 2/2016 | Sumihiro | F25D 11/00 62/125 |
| 2017/0130981 A1 | 5/2017 | Willette et al. | |
| 2017/0318986 A1 * | 11/2017 | Santarelli | F16M 13/022 |
| 2017/0350147 A1 * | 12/2017 | Janko | A47G 3/00 |
| 2018/0154297 A1 | 6/2018 | Maletich et al. | |
| 2018/0344890 A1 | 12/2018 | Watanabe et al. | |
| 2019/0125917 A1 | 5/2019 | Kim et al. | |
| 2020/0340507 A1 * | 10/2020 | Kehdy | F16M 11/041 |

FOREIGN PATENT DOCUMENTS

| | | |
|---|---|---|
| JP | S60-001360 U | 1/1985 |
| JP | H04-091495 U | 8/1992 |
| JP | 3097434 U | 1/2004 |
| JP | 2012-095972 | 5/2012 |
| JP | 2014-219130 | 11/2014 |
| JP | 2017-148484 | 8/2017 |
| JP | 2019-017855 | 2/2019 |
| JP | 2019-513970 | 5/2019 |
| KR | 10-2009-0078908 | 7/2009 |
| WO | 2015/177842 | 11/2015 |
| WO | 2017/088356 | 6/2017 |
| WO | 2017/209776 | 12/2017 |

* cited by examiner

[Fig. 1]
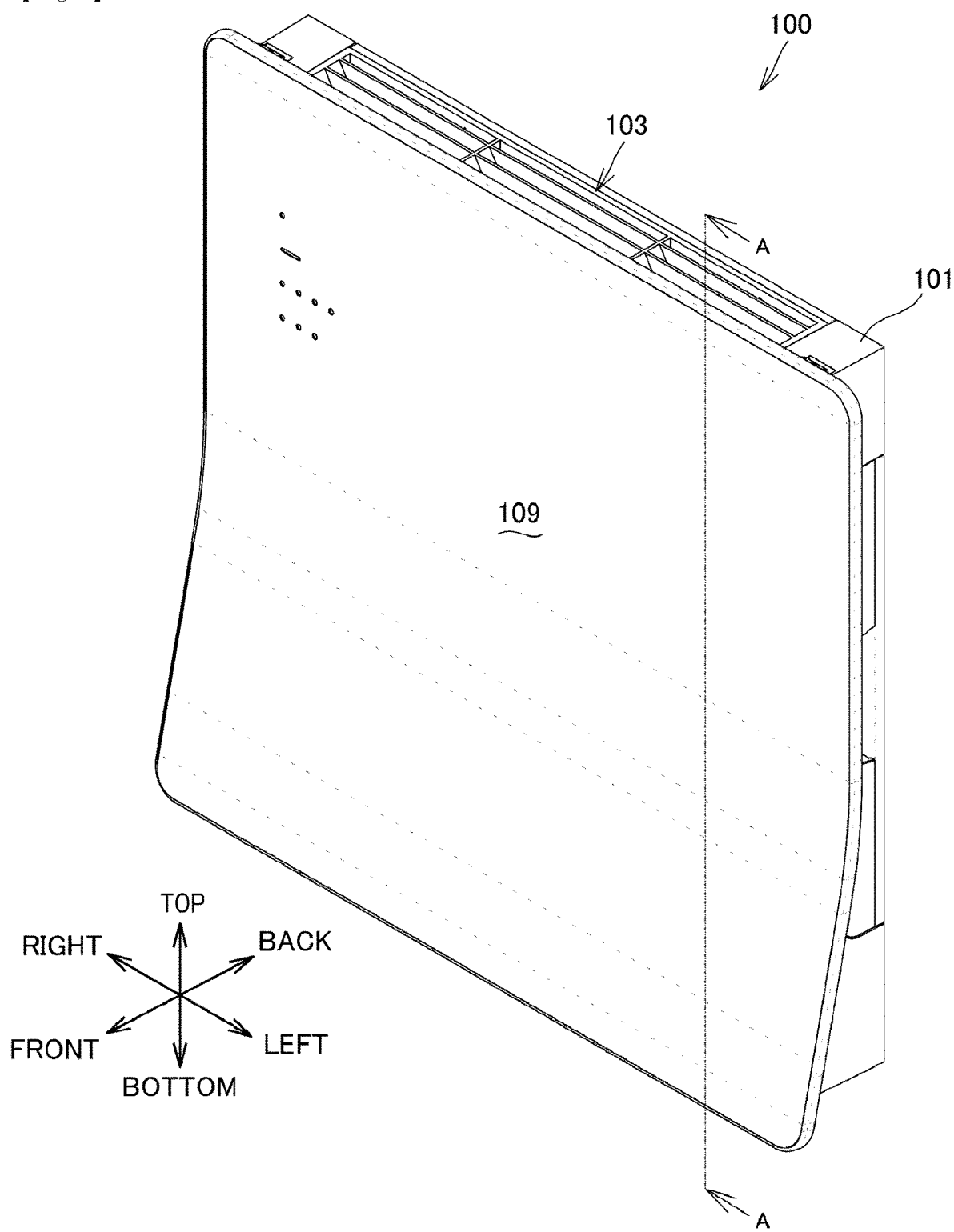

[Fig. 2]
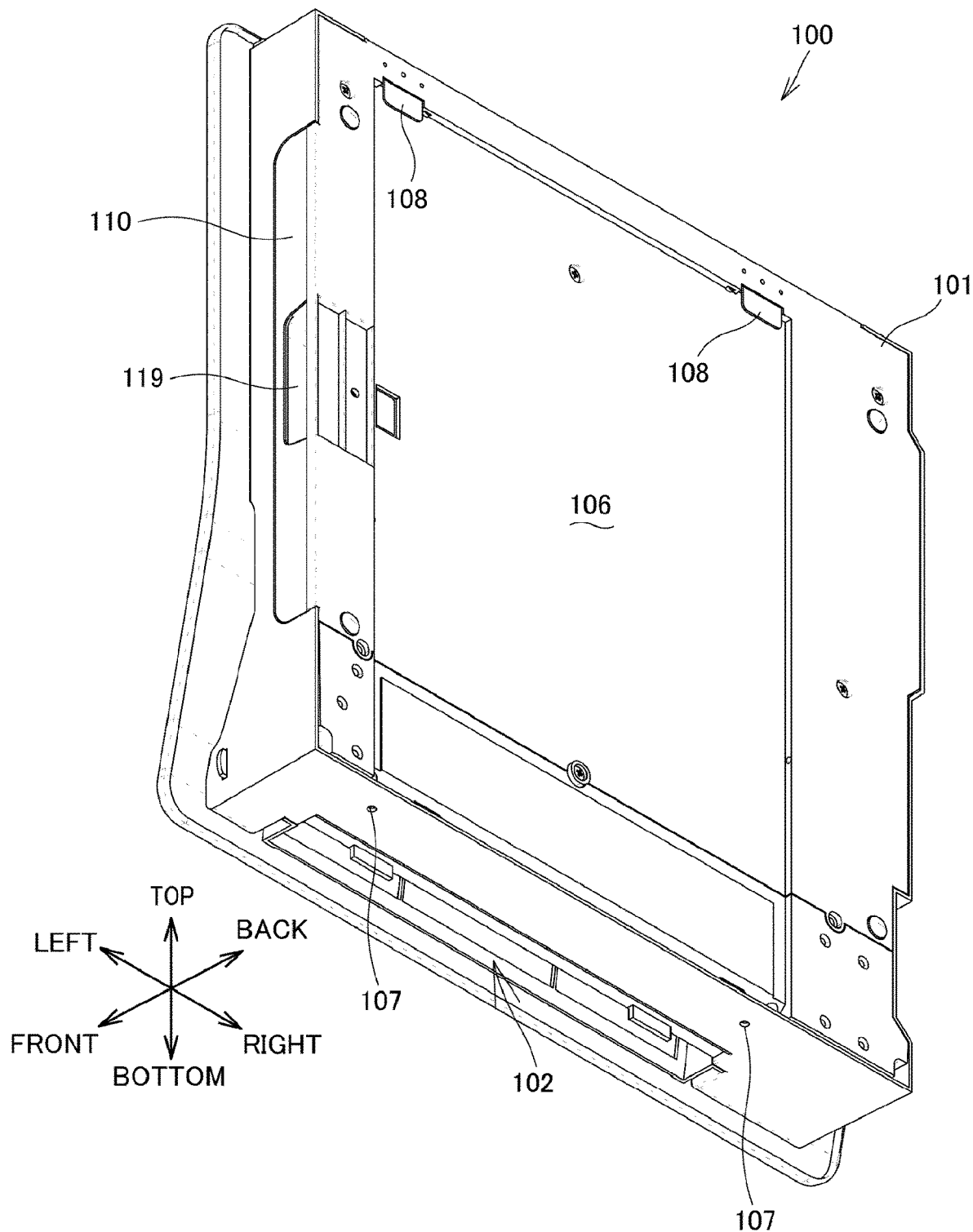

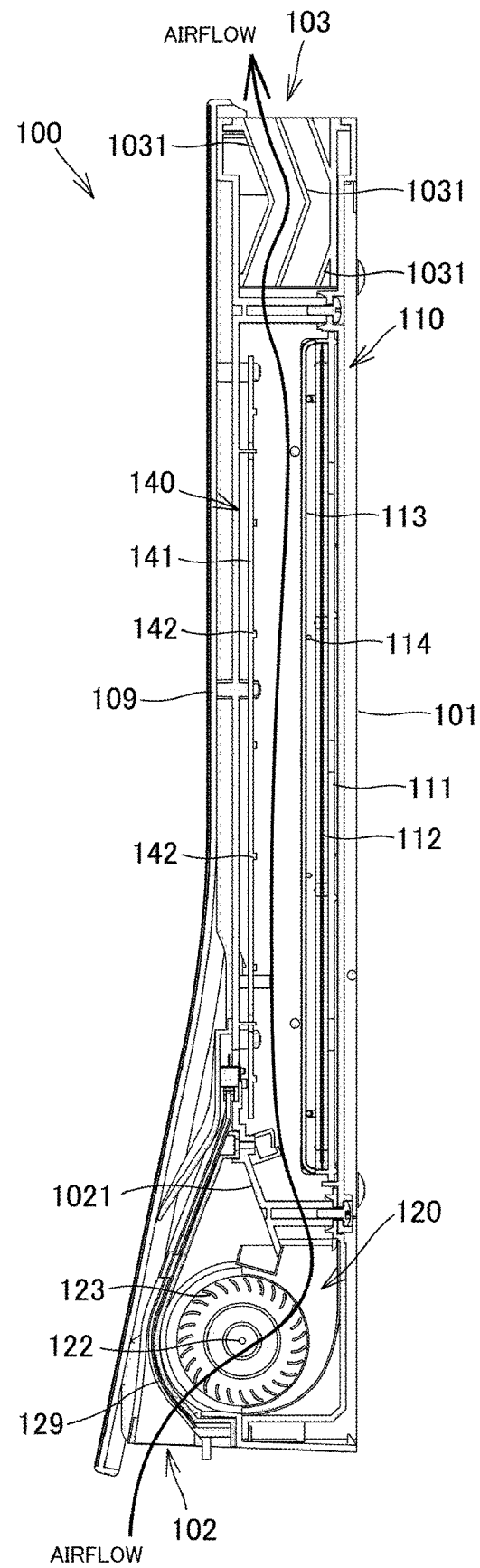
[Fig. 3]

[Fig. 4]
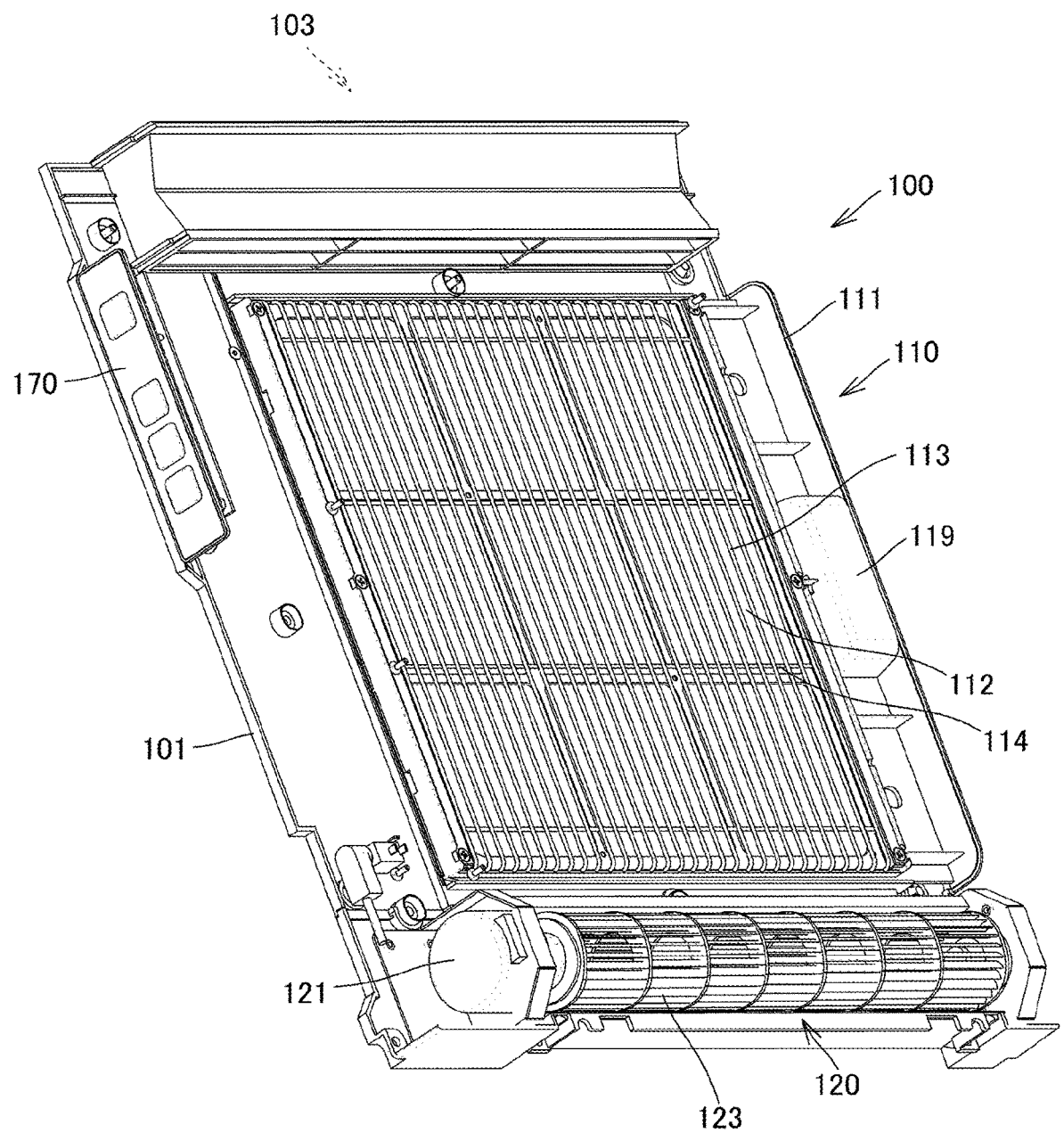

[Fig. 5]
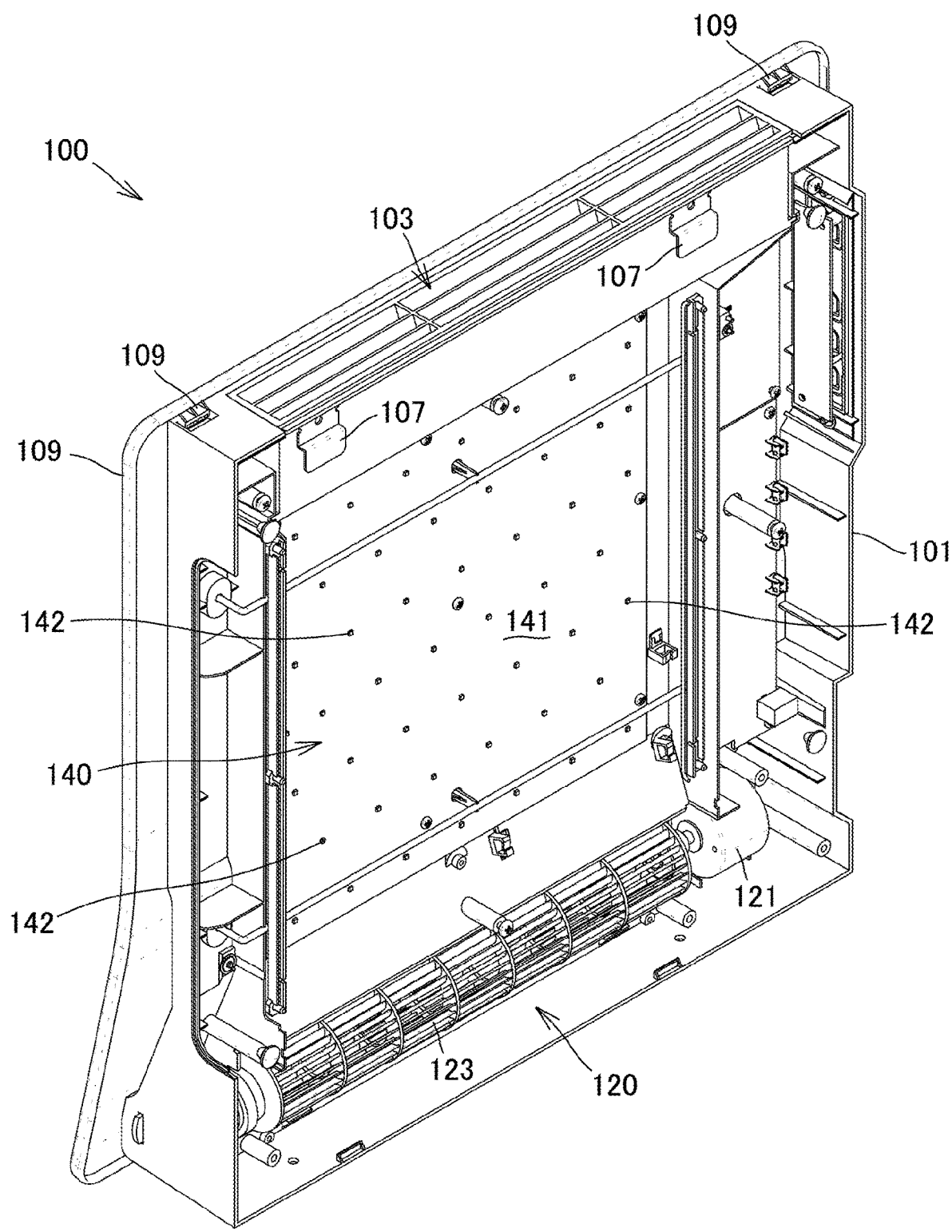

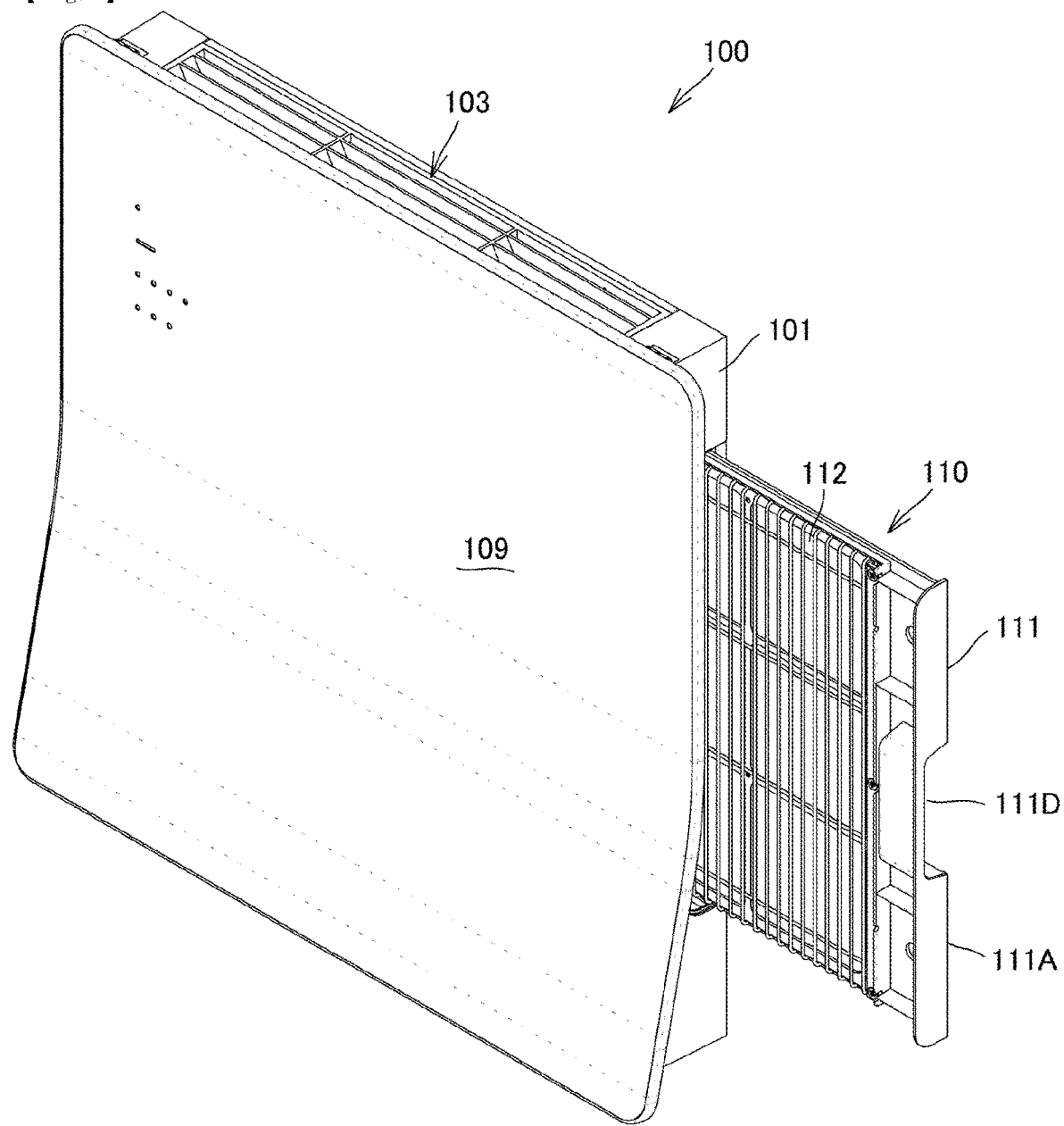
[Fig. 6]

[Fig. 7]
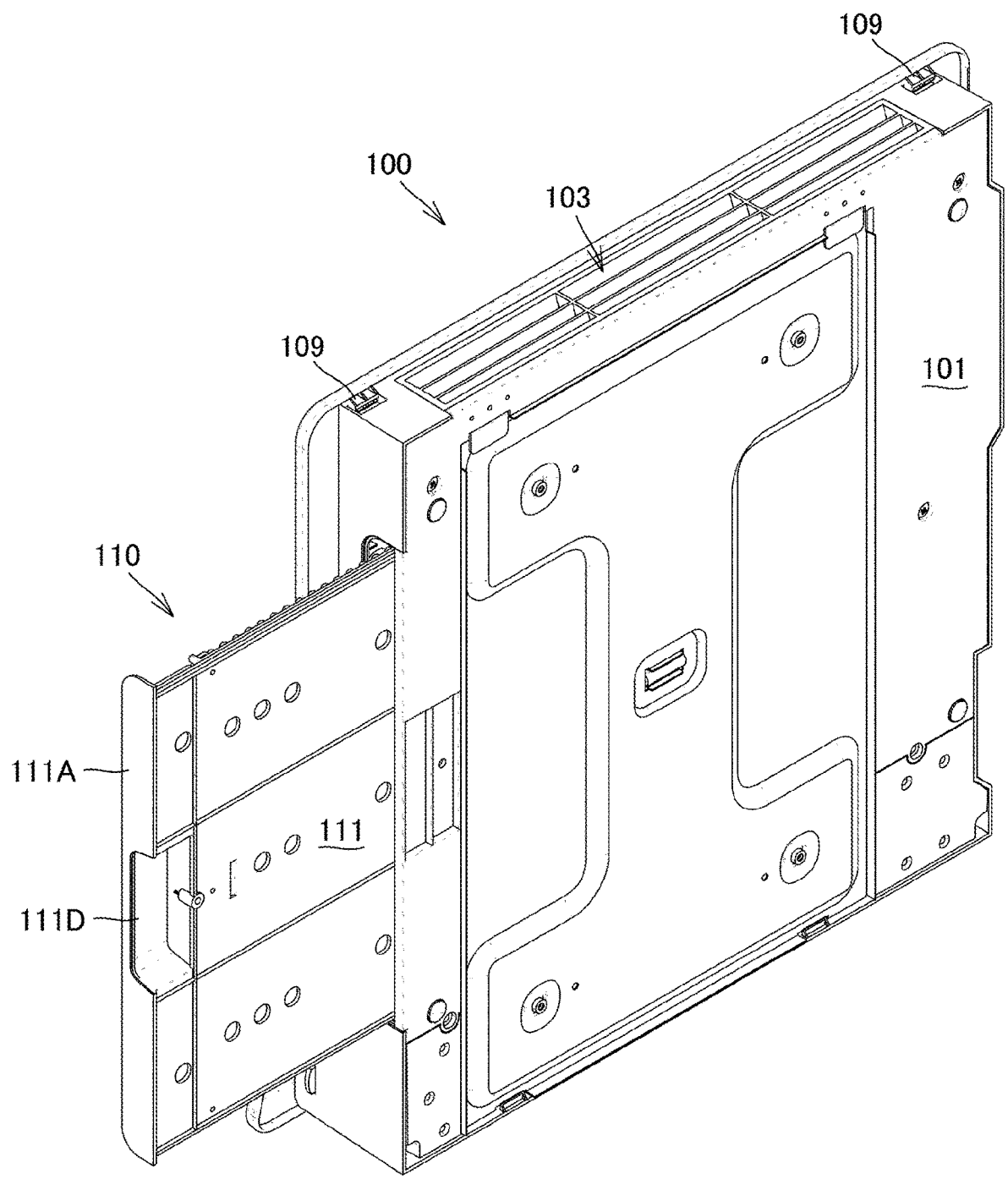

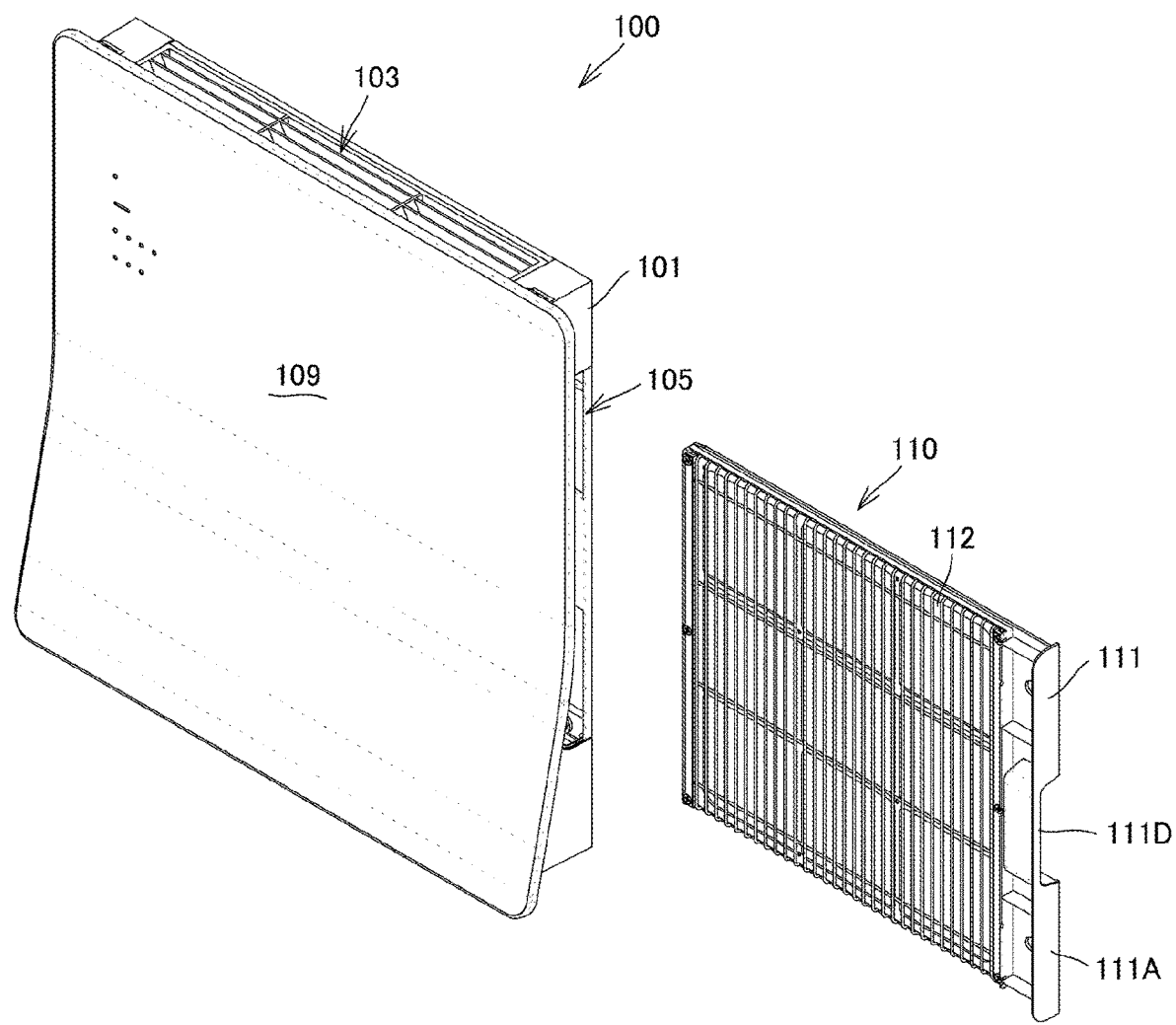
[Fig. 8]

[Fig. 9]
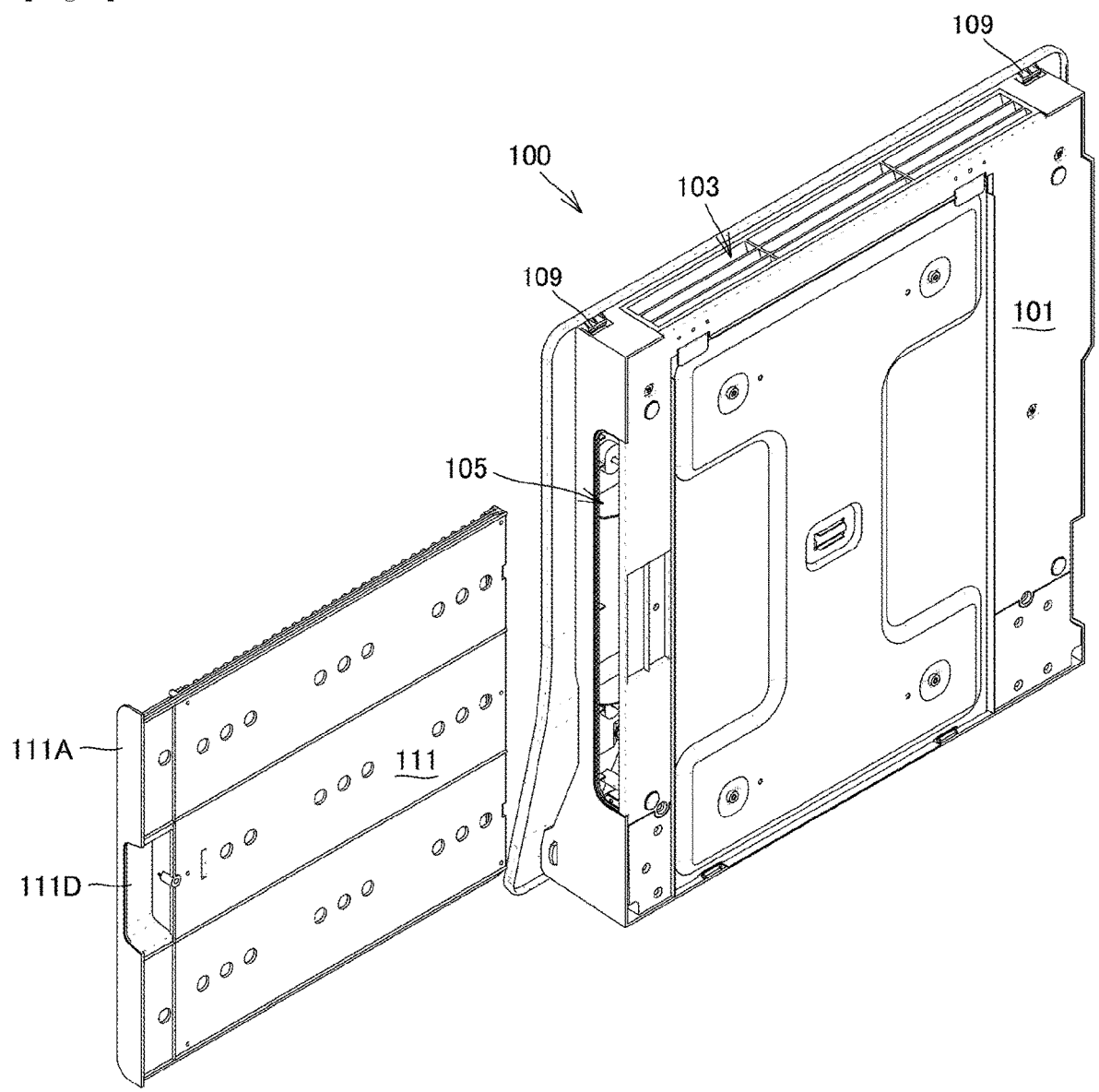

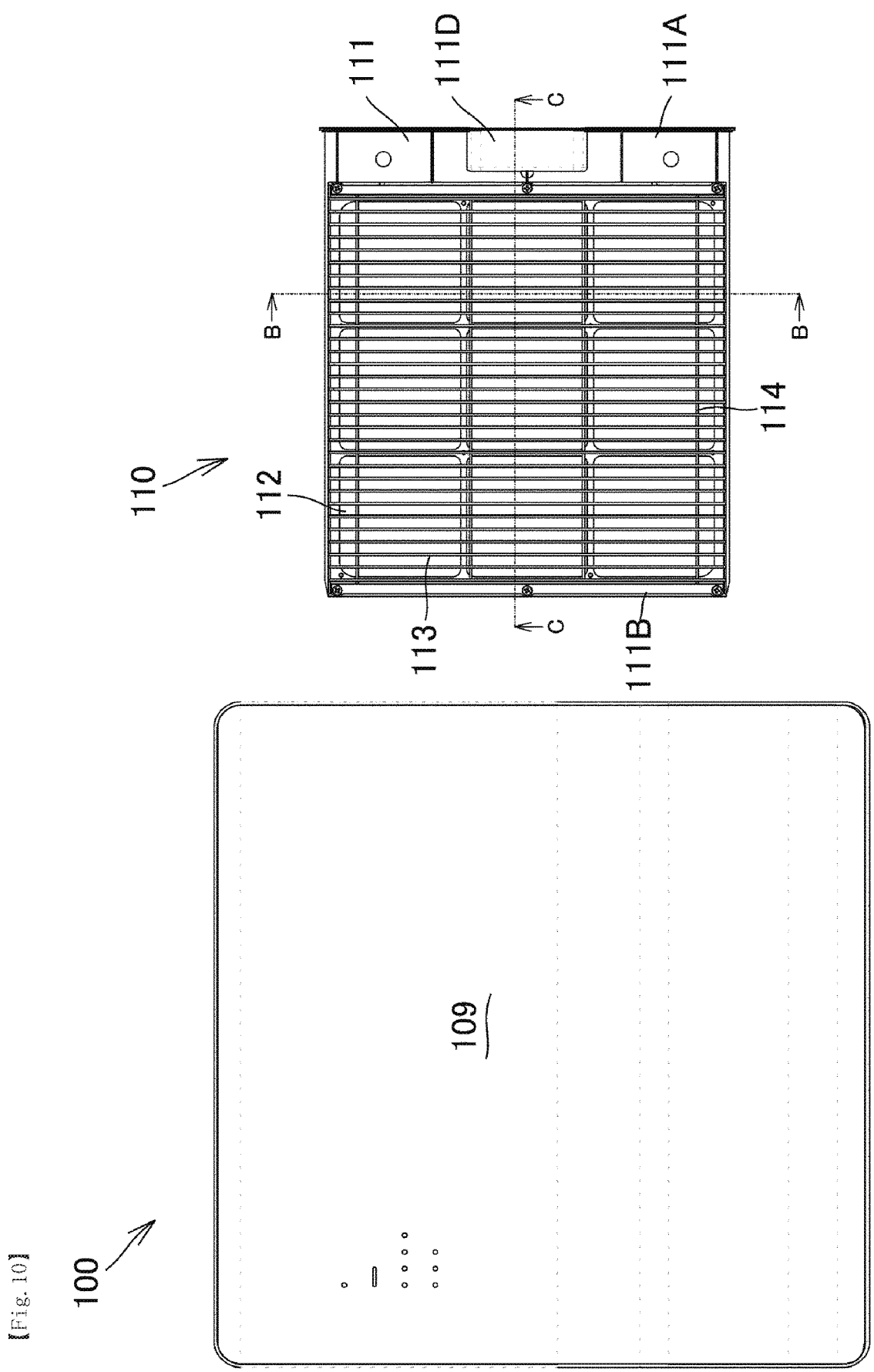

[Fig. 11]
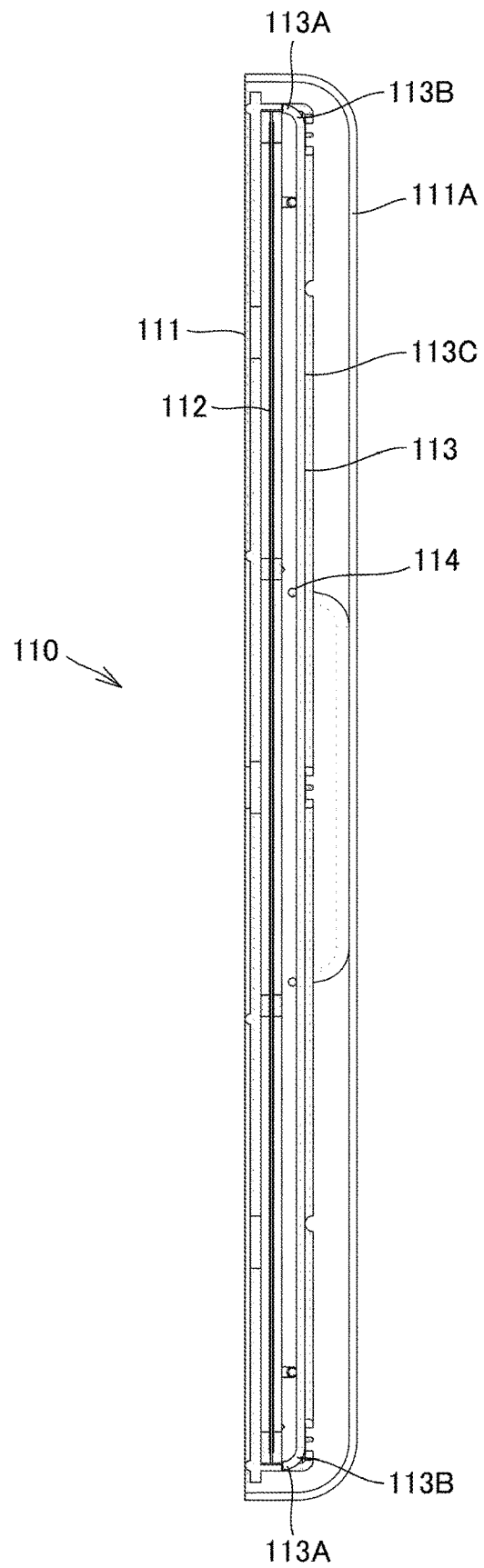

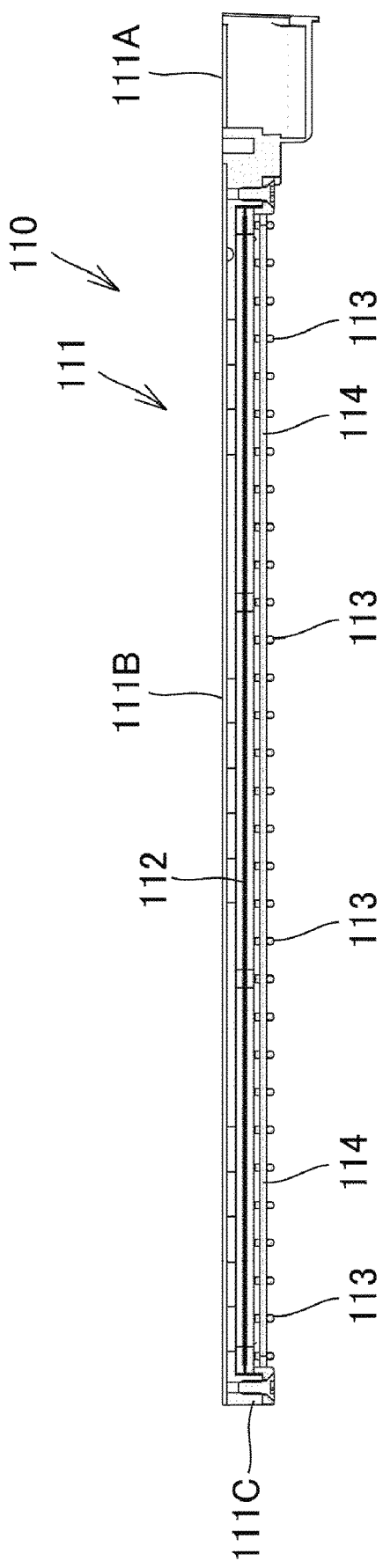
[Fig. 12]

[Fig. 13]
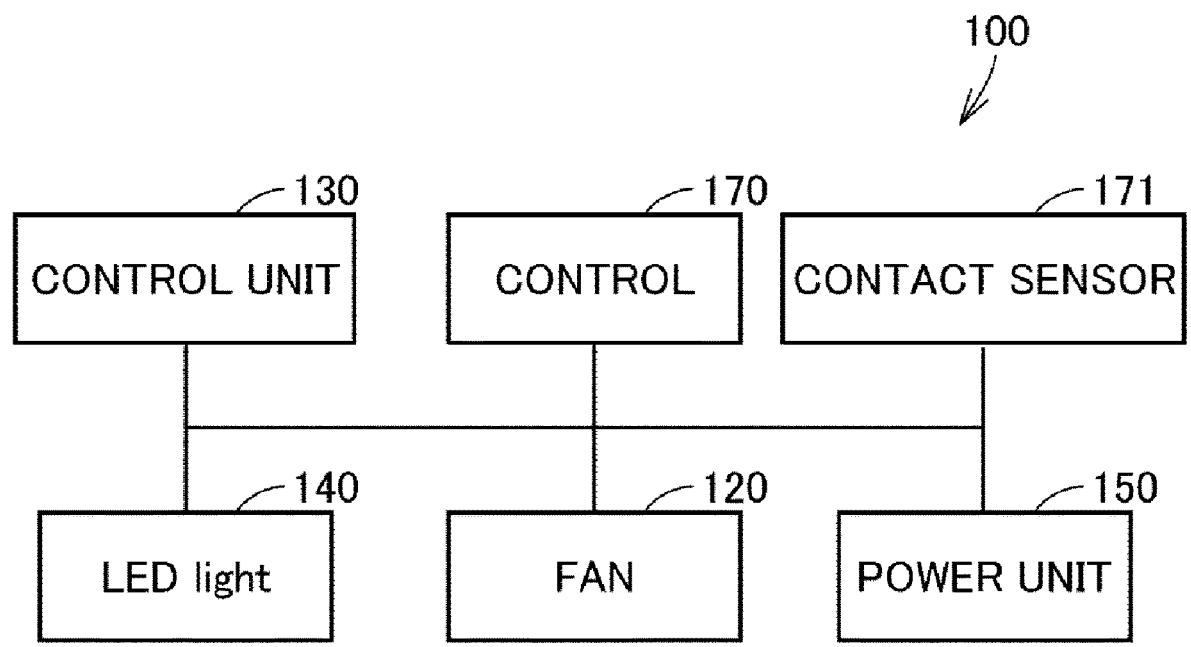

[Fig. 14]
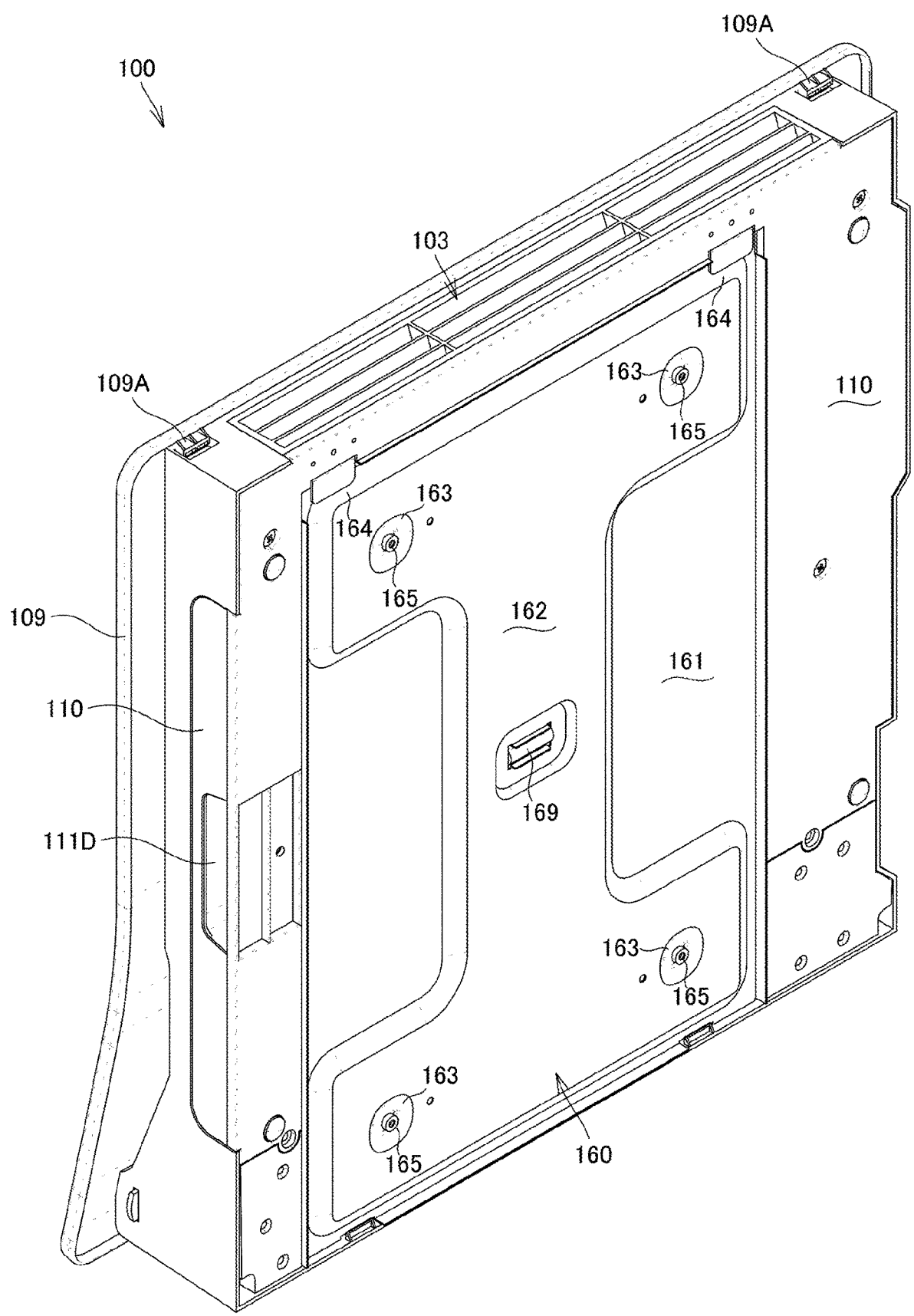

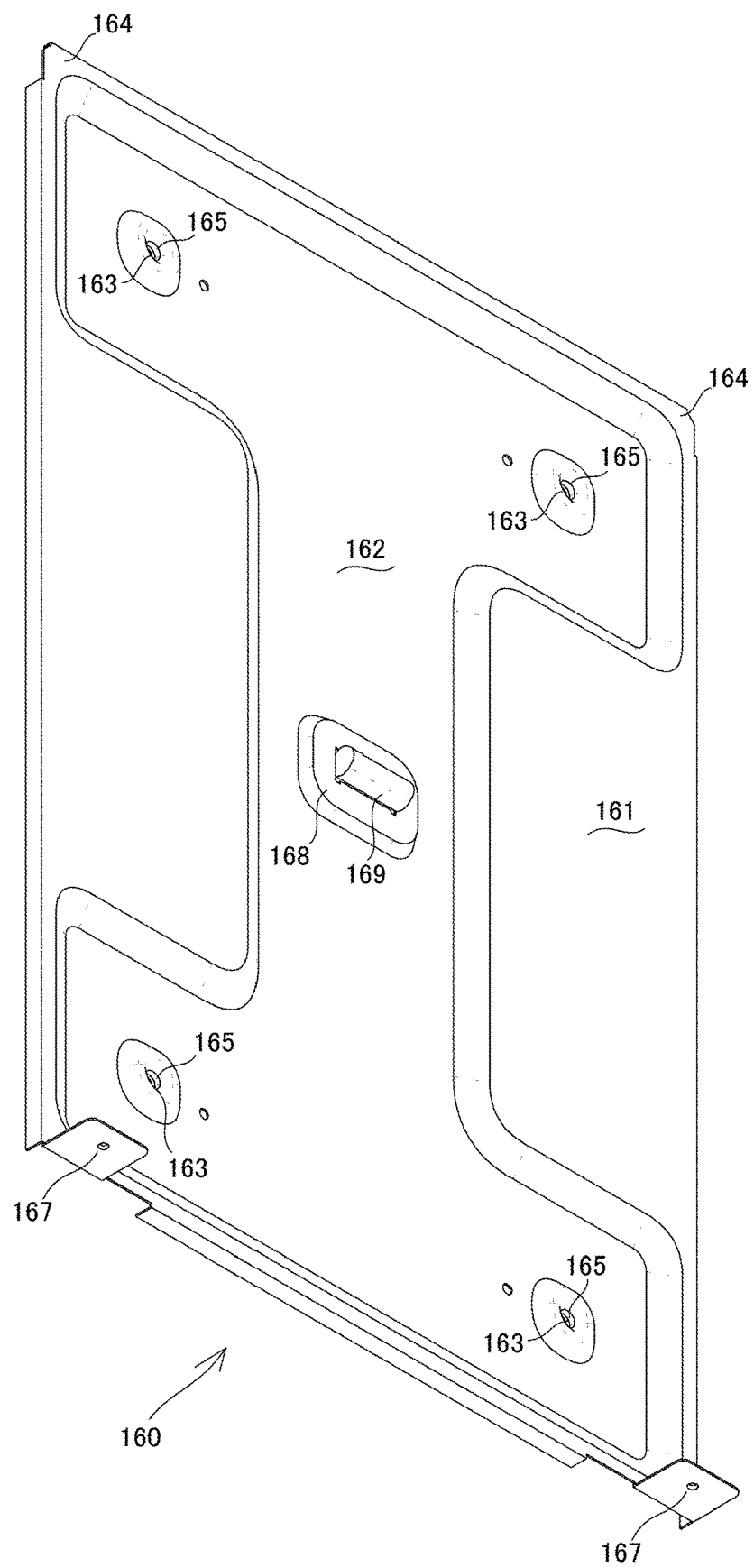
[Fig. 15]

[Fig. 16]
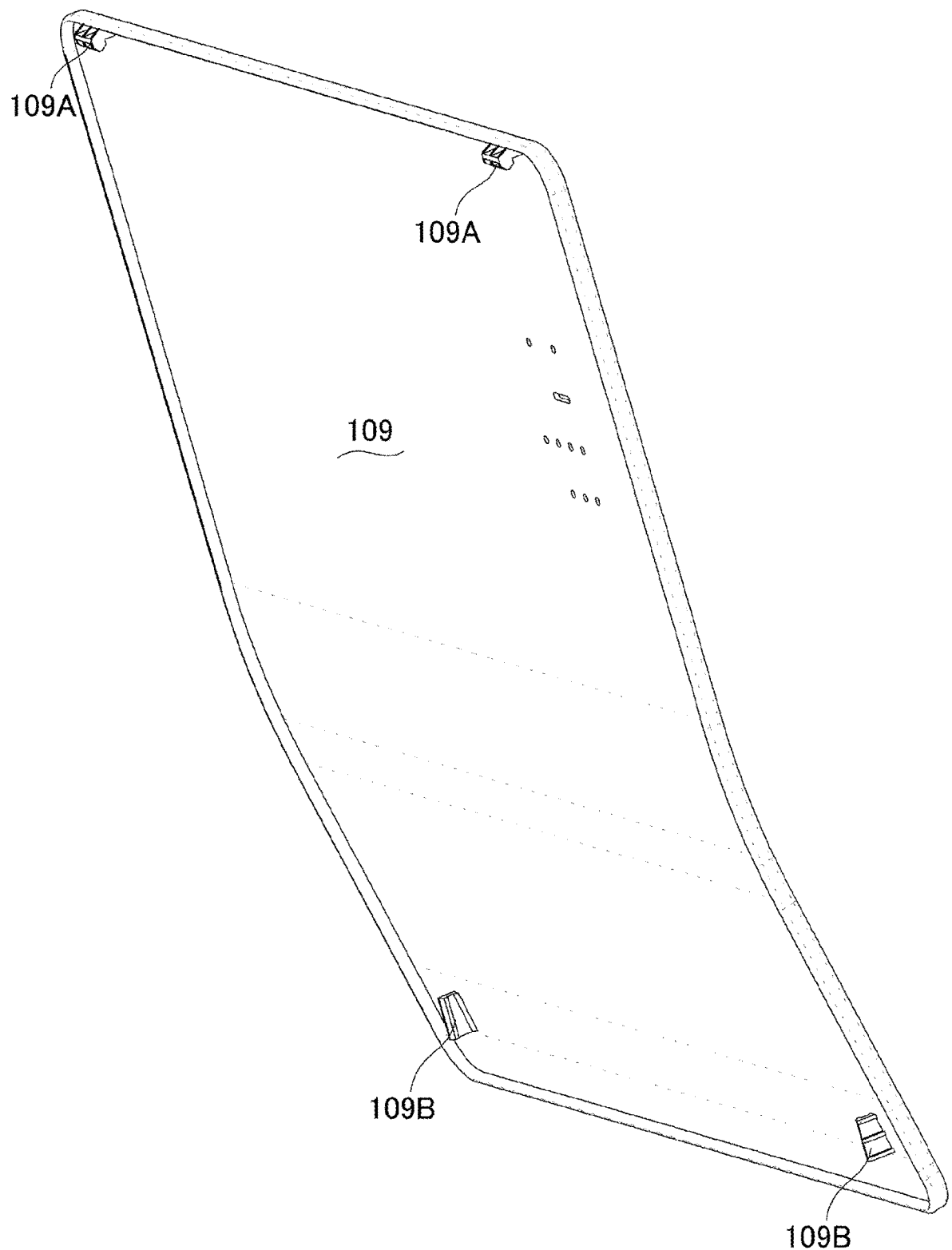

[Fig. 17]
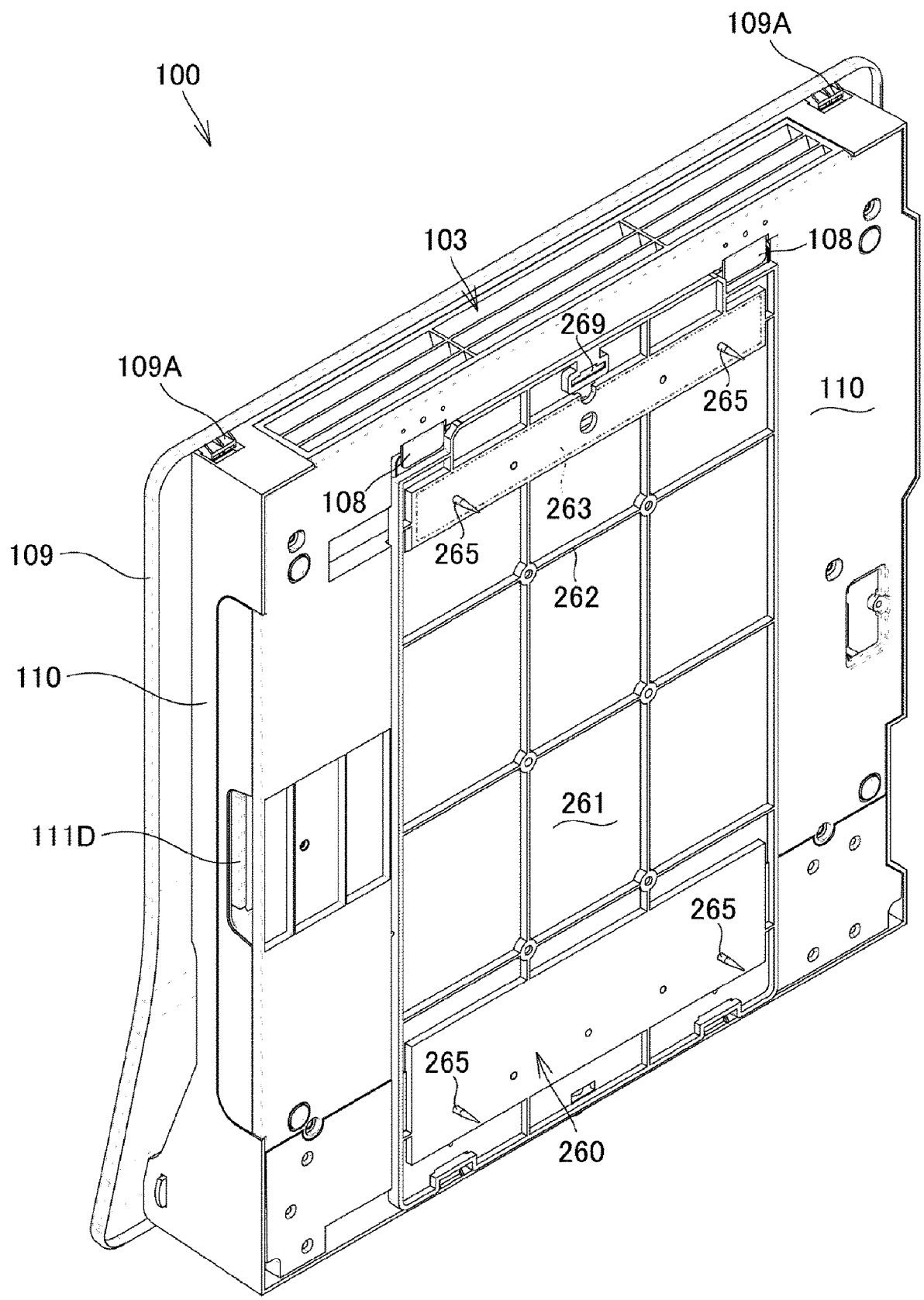

[Fig. 18]
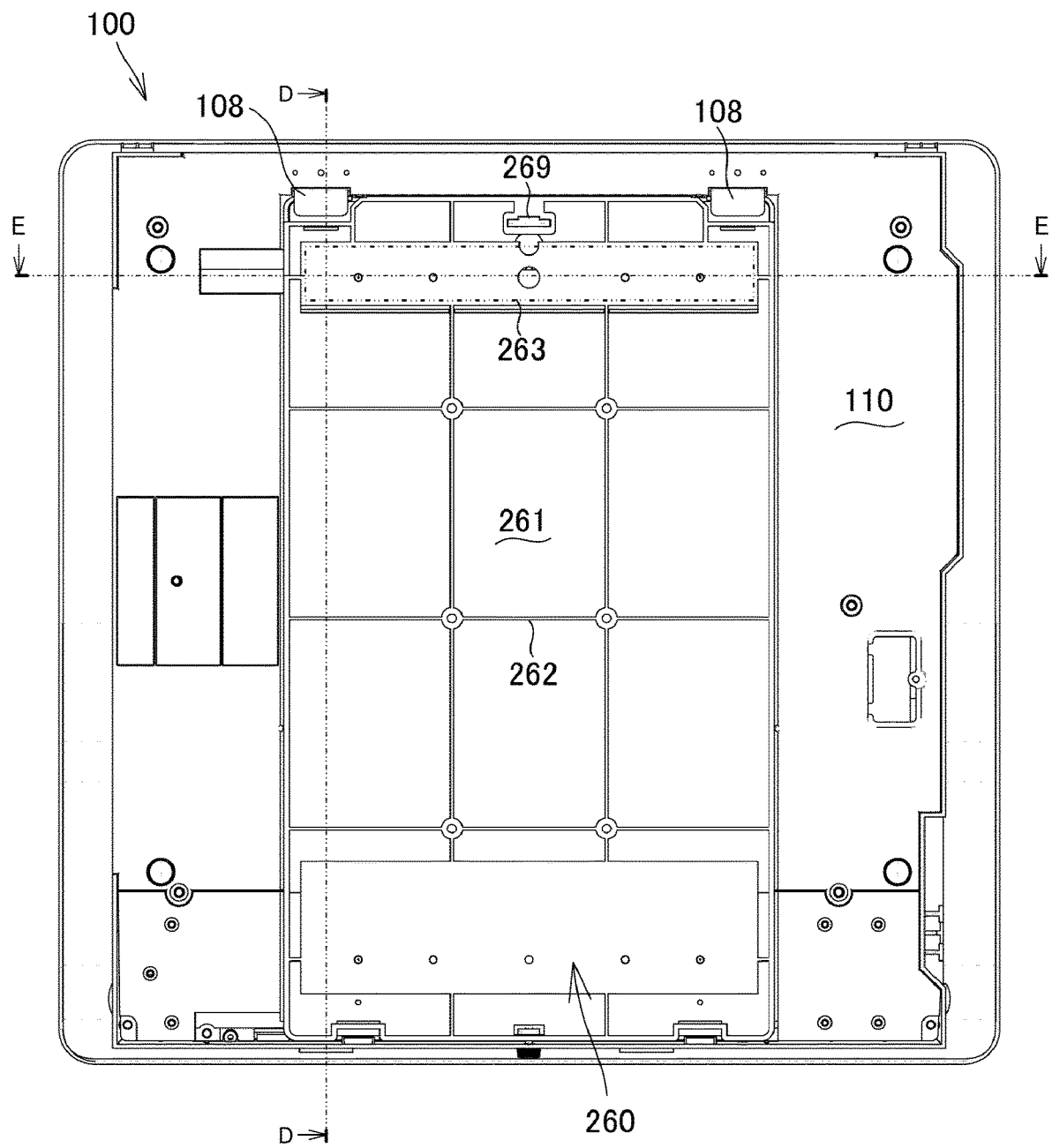

[Fig. 19]
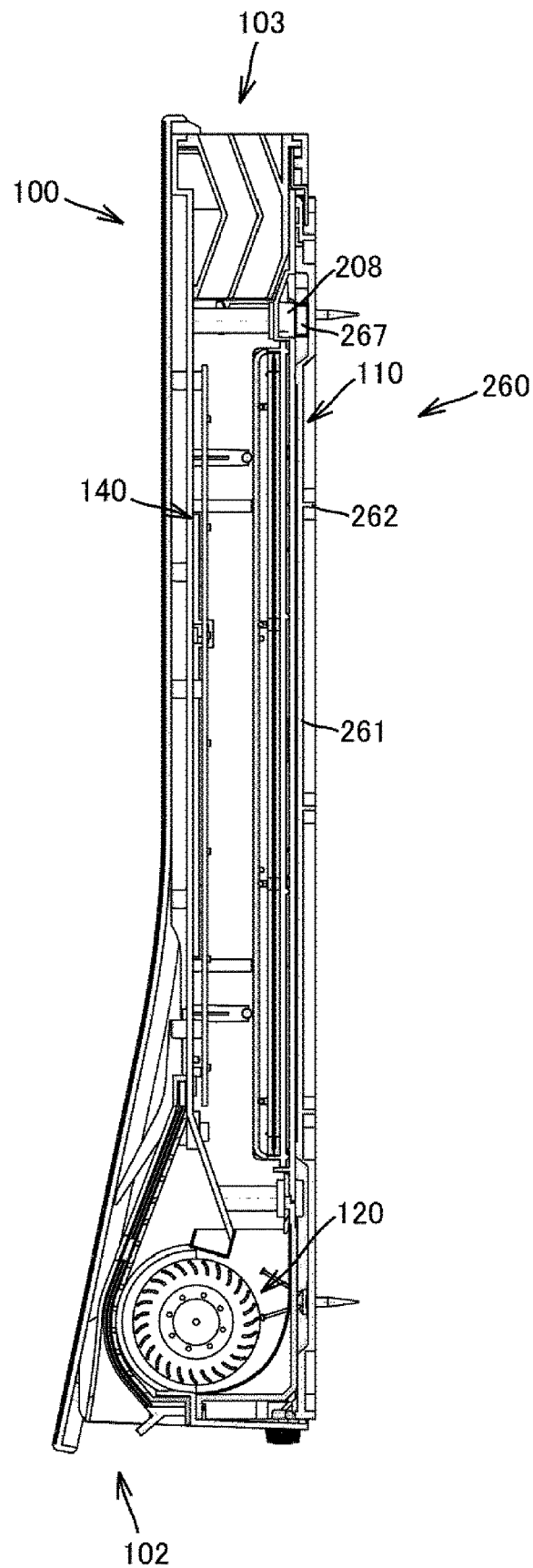

[Fig. 20]
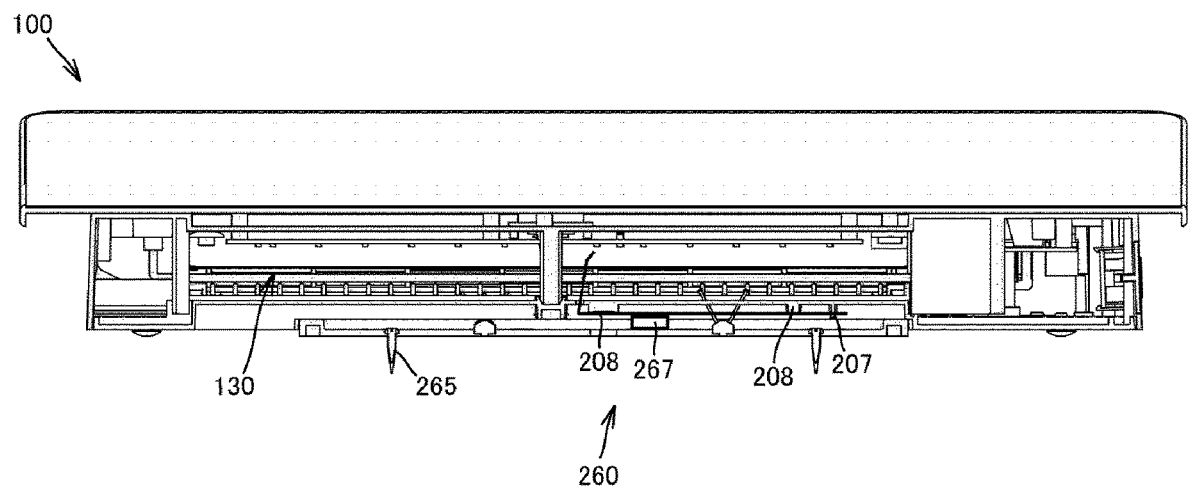

[Fig. 21]
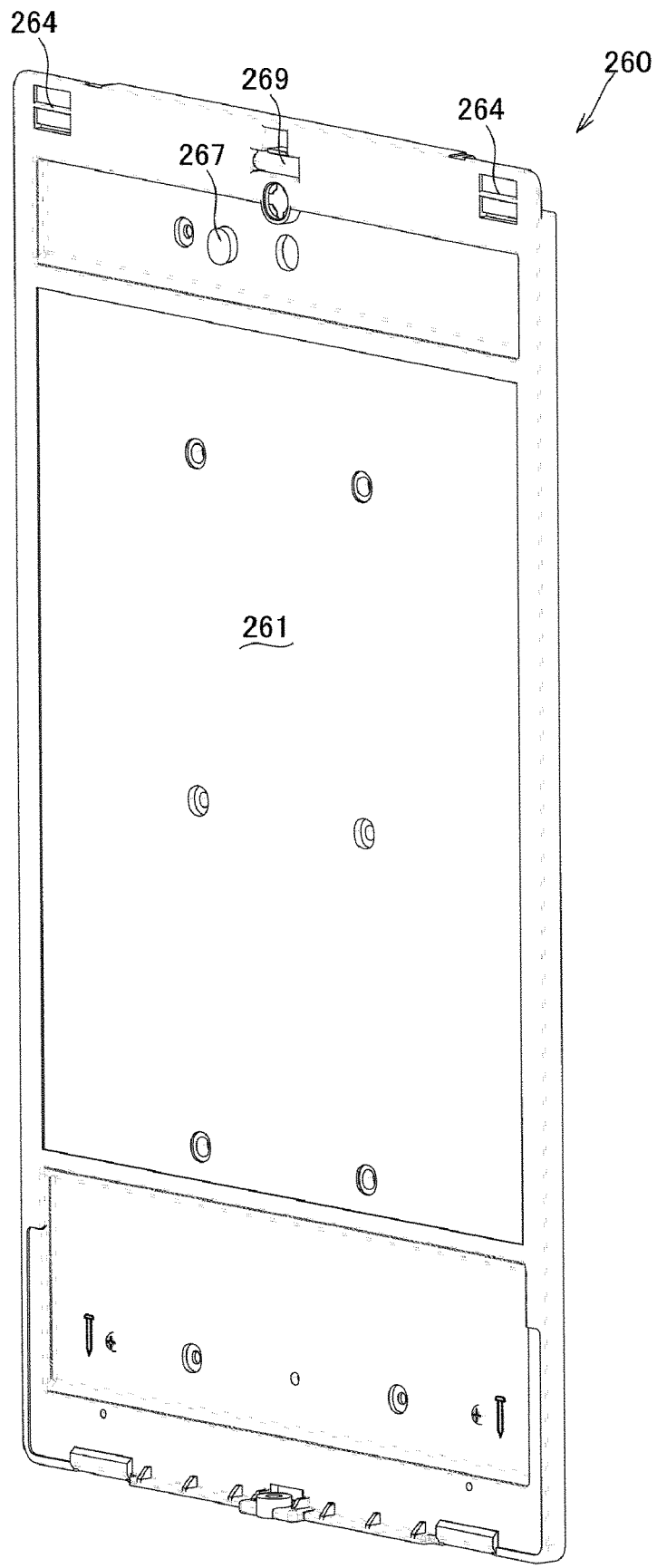

[Fig. 22]
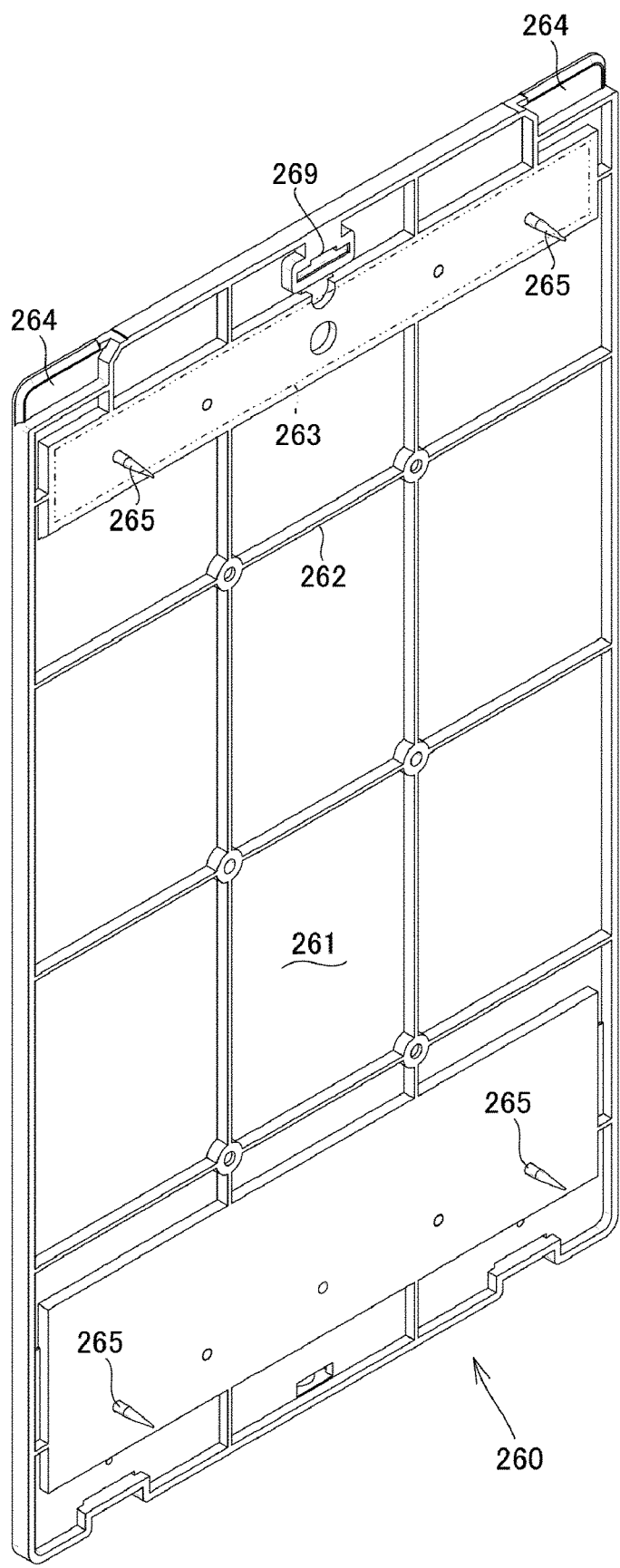

[Fig. 23]
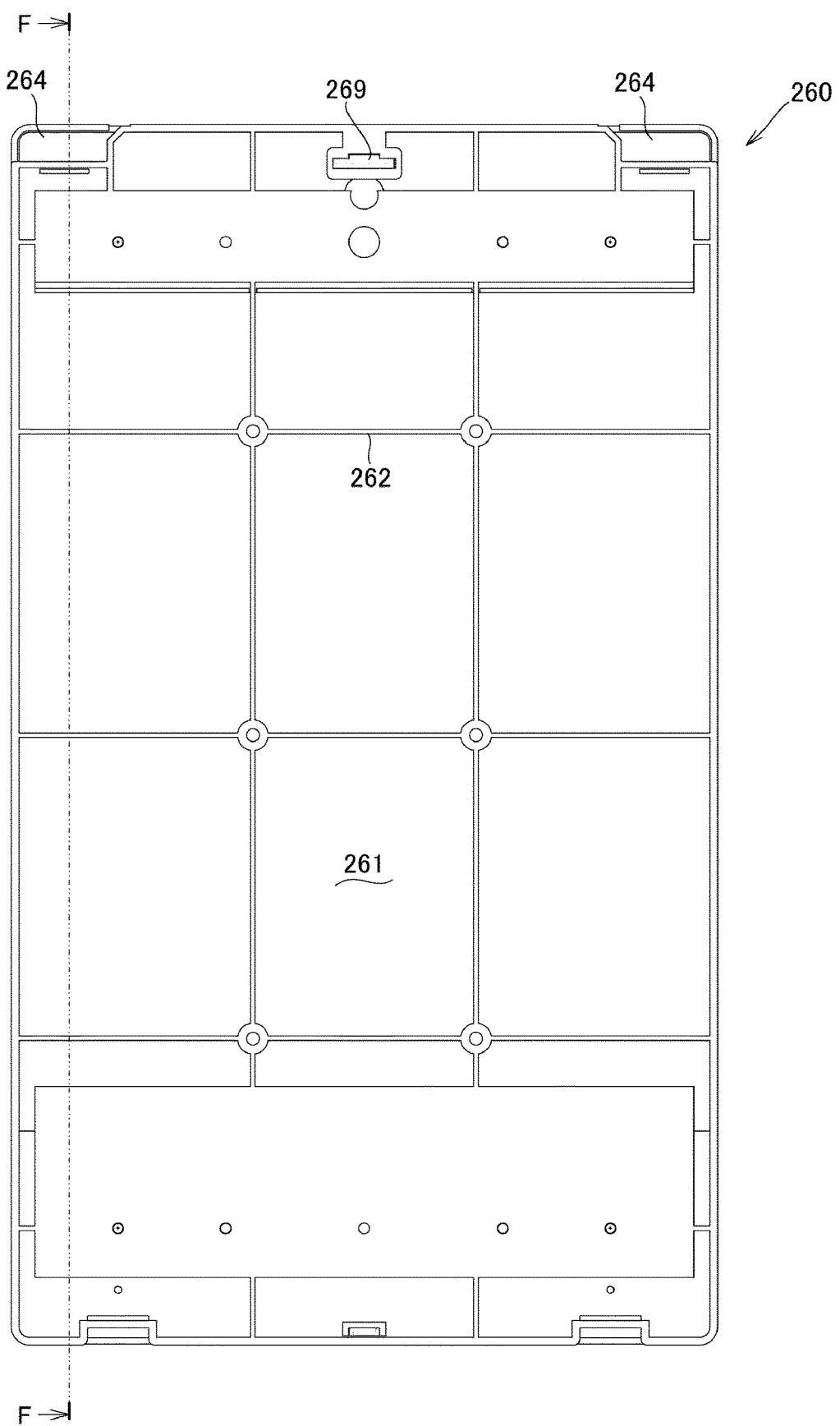

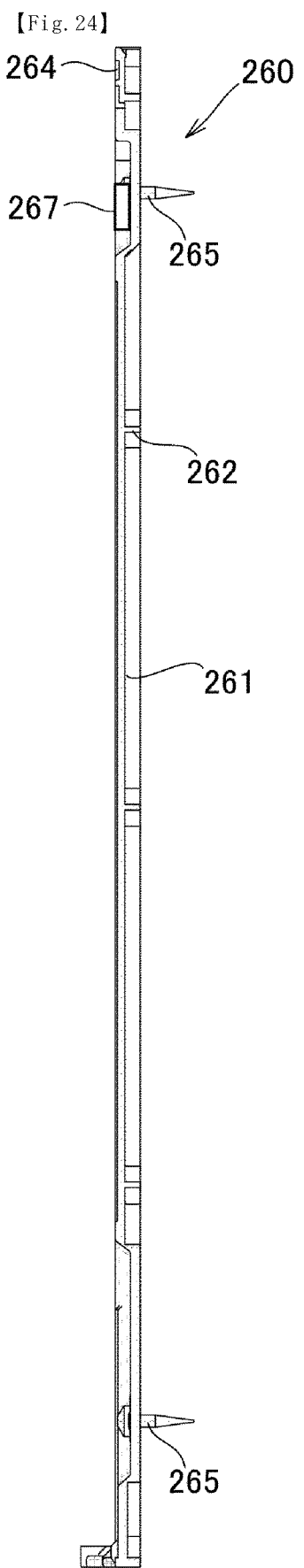
[Fig. 24]

[Fig. 25]
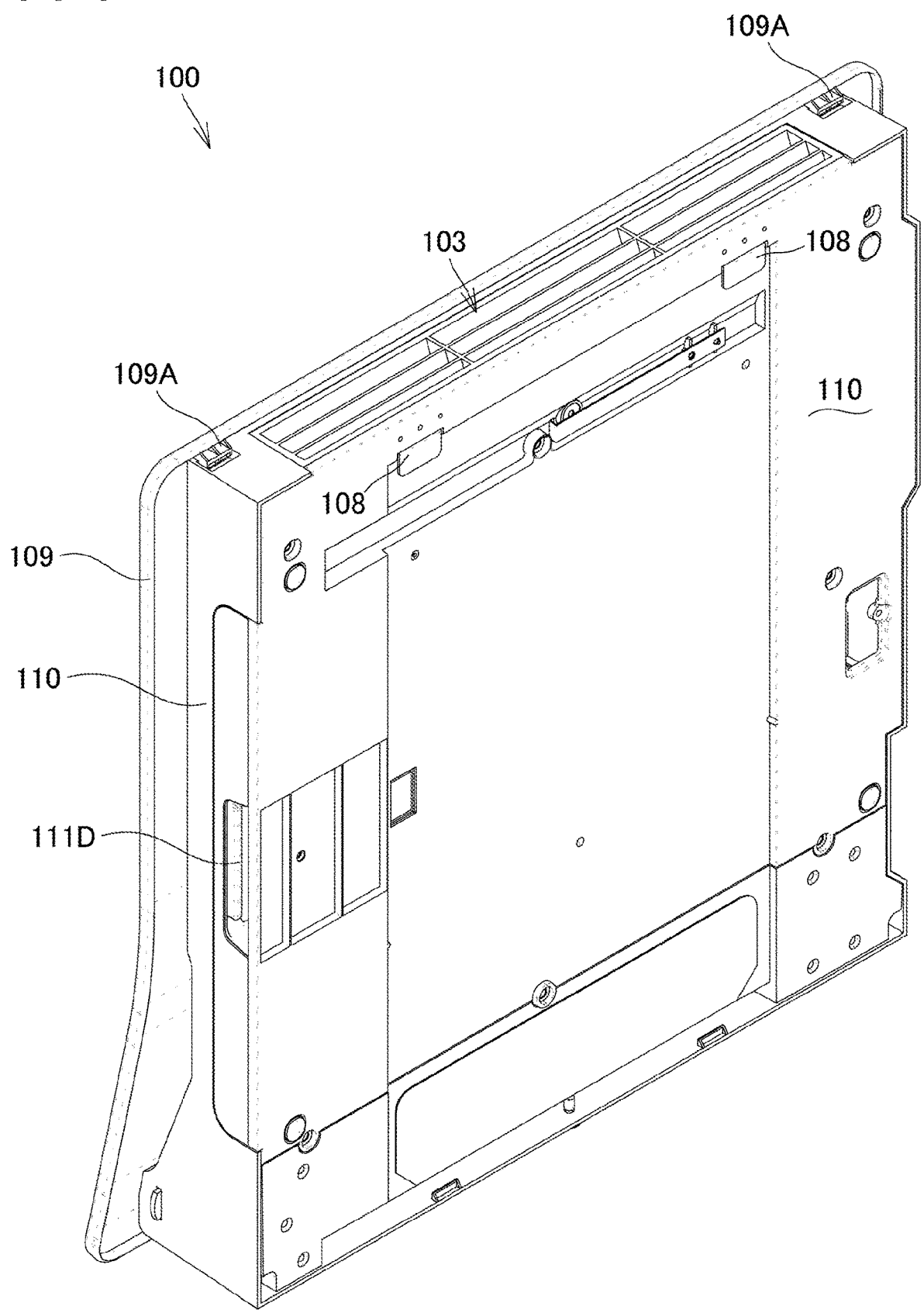

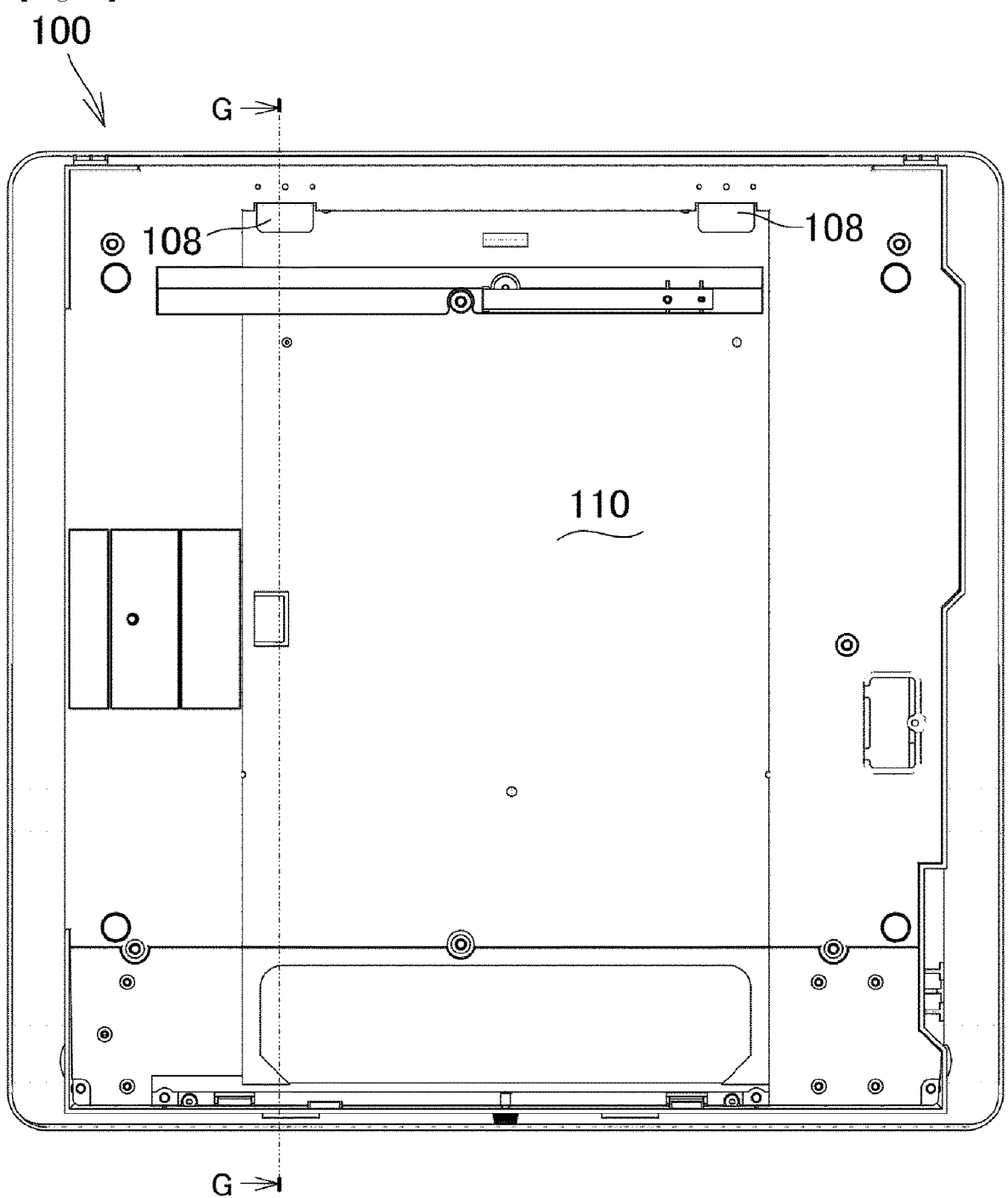
[Fig. 26]

[Fig. 27]
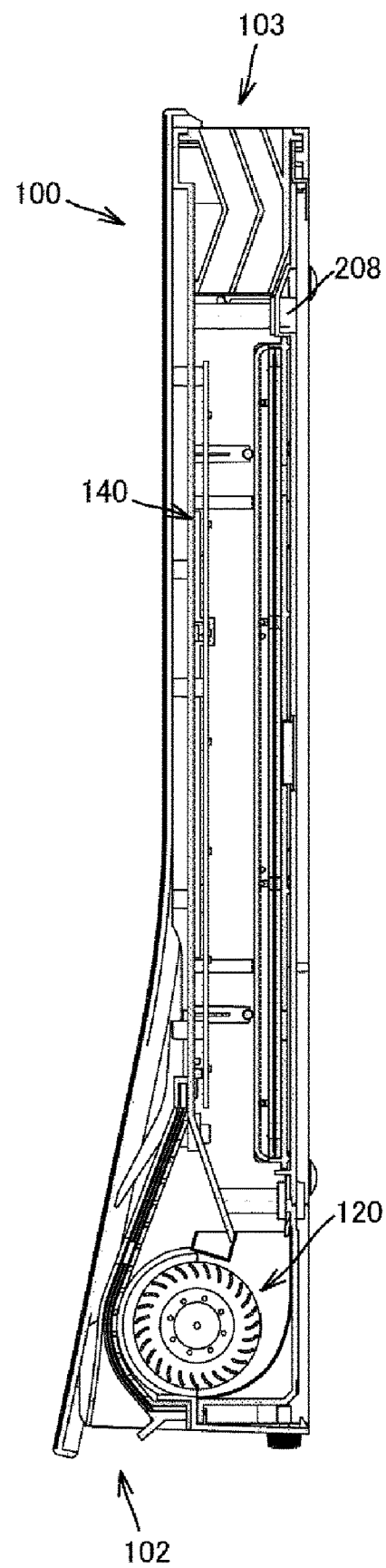

[Fig. 28]
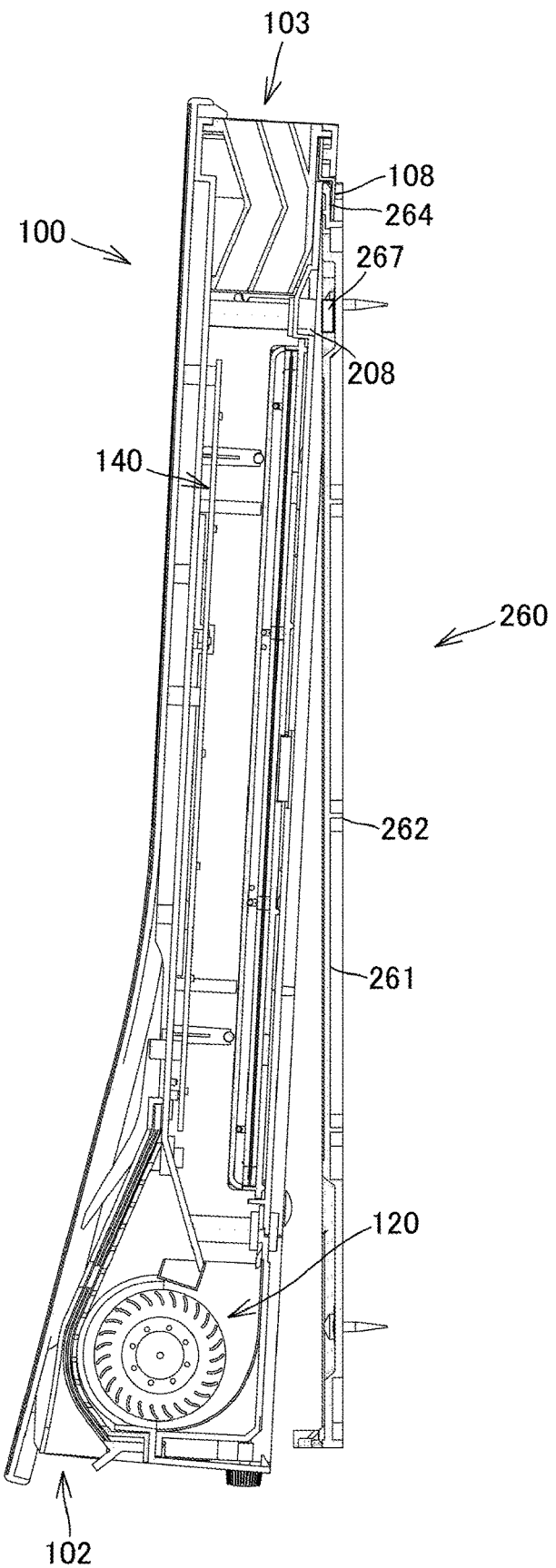

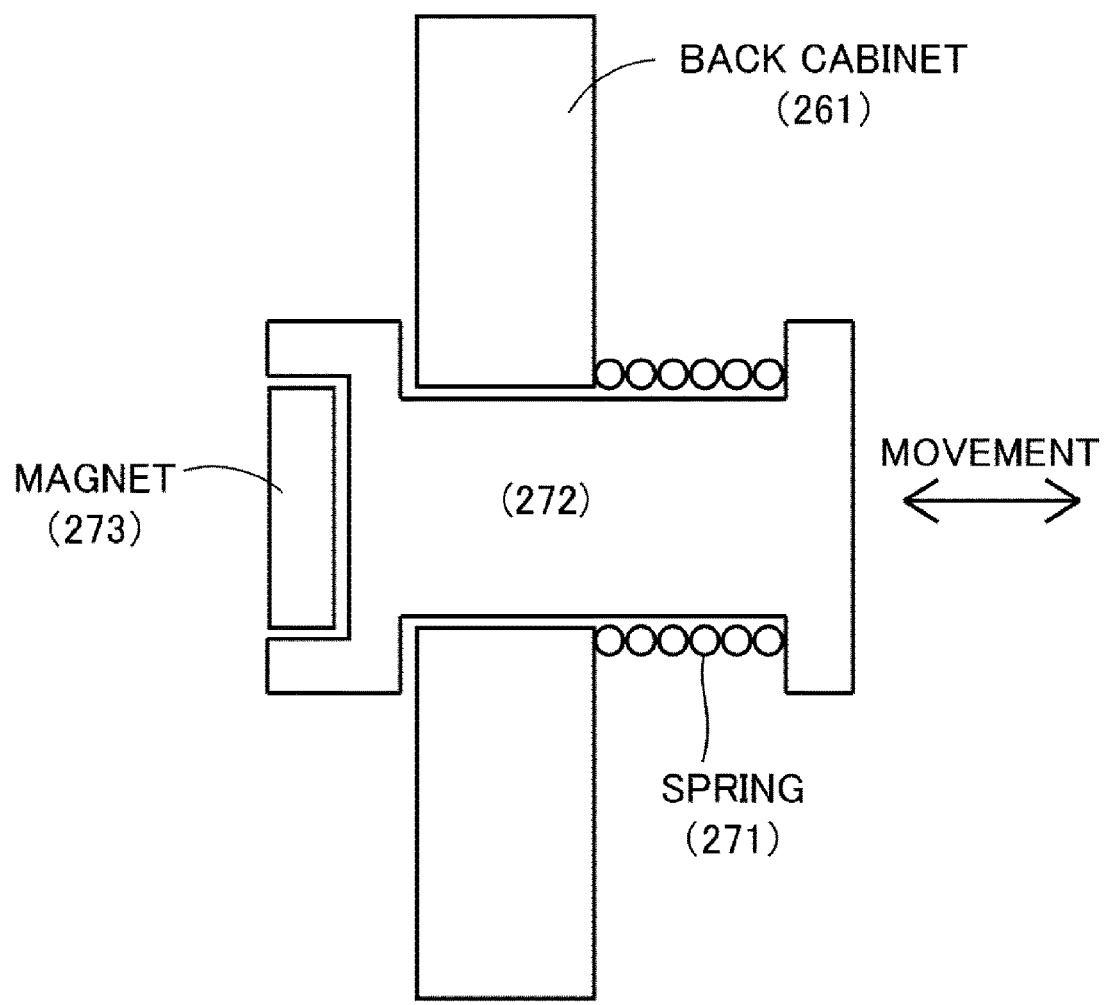

US 11,448,245 B2

WALL ATTACHMENT SYSTEM

BACKGROUND OF THE INVENTION

Field of the Invention

The present invention relates to a technology for attaching an object to be mounted such as a deodorization device to a wall surface.

Description of the Related Art

Photocatalytic devices are known that are intended for deodorization and sterilization of air. For example, JP-A-2014-219130 discloses a refrigerator using a photocatalyst. In the refrigerator disclosed in JP-A-2014-219130, a catalyst base supporting a photocatalyst is attached in such an orientation that the photocatalyst is exposed to the storage compartment side of a back panel constituting a cold air passage, and a light emitting diode is provided on the inner surface of an inner box constituting the cold air passage so as to emit light toward the catalyst base. With the catalyst base provided as a part of the back panel, and the photocatalyst excited by the light emitting diode provided on the inner box, the catalyst base can be sized as desired to ensure a sufficient catalyst area. This enables effective removal of odor components and sterilization in a large-volume storage compartment. Another advantage is that the carbon dioxide generated by the catalytic action of the photocatalyst can reduce the oxygen concentration in the storage compartment, keeping vegetables fresh for a longer time period by inhibiting the breathing of vegetables.

SUMMARY OF INVENTION

An object of the present invention is to provide a technology for conveniently attaching an object to be mounted such as a deodorization device to a wall surface.

According to a certain aspect of the present invention, there is provided a wall attachment system that includes an object to be mounted, and an attachment unit for attaching the object to be mounted to a wall surface. The object to be mounted has aback surface installed with a metal. The attachment unit has a front surface installed with a magnet. The wall attachment system is configured so that the metal and the magnet contact each other in response to the object to be mounted being set in position for installation on the attachment unit.

It can thus be seen that the present invention has provided a technology for conveniently attaching an object to be mounted such as a deodorization device to a wall surface.

BRIEF DESCRIPTION OF THE DRAWINGS

FIG. 1 is a front perspective view showing the exterior of a photocatalytic device according to First Embodiment.

FIG. 2 is a rear perspective view showing the exterior of the photocatalytic device according to First Embodiment.

FIG. 3 is a vertical cross sectional view showing the interior of the photocatalytic device according to First Embodiment, specifically, across sectional view at A-A of FIG. 1.

FIG. 4 is a front perspective view showing inside of the photocatalytic device according to First Embodiment, specifically, the photocatalytic device after the removal of a front panel, a front part of a cabinet, and an LED light.

FIG. 5 is a front perspective view showing inside of the photocatalytic device according to First Embodiment, specifically, the photocatalytic device after the removal of a rear part of the cabinet, and a photocatalytic unit.

FIG. 6 is a front perspective view showing a state after the photocatalytic unit is partly pulled out from the cabinet according to First Embodiment.

FIG. 7 is a rear perspective view showing a state after the photocatalytic unit is partly pulled out from the cabinet according to First Embodiment.

FIG. 8 is a front perspective view showing a state after the photocatalytic unit is fully pulled out from the cabinet according to First Embodiment.

FIG. 9 is a rear perspective view showing a state after the photocatalytic unit is fully pulled out from the cabinet according to First Embodiment.

FIG. 10 is a front view showing a state after the photocatalytic unit is fully pulled out from the cabinet according to First Embodiment.

FIG. 11 is a vertical cross sectional view of the photocatalytic unit according to First Embodiment, specifically, a cross sectional view at B-B of FIG. 10.

FIG. 12 is a horizontal cross sectional view of the photocatalytic unit according to First Embodiment, specifically, a cross sectional view at C-C of FIG. 10.

FIG. 13 is a functional block diagram representing a configuration of the photocatalytic device according to First Embodiment.

FIG. 14 is a rear perspective view of a photocatalytic device, showing a state after the photocatalytic device is attached to an attachment unit according to First Embodiment.

FIG. 15 is a front perspective view of the attachment unit according to First Embodiment.

FIG. 16 is a rear perspective view of a front panel according to First Embodiment.

FIG. 17 is a rear perspective view of a photocatalytic device after being attached to an attachment unit according to Fourth Embodiment.

FIG. 18 is a rear view of a photocatalytic device after being attached to the attachment unit according to Fourth Embodiment.

FIG. 19 is a vertical cross sectional view of a photocatalytic device after being attached to the attachment unit according to Fourth Embodiment, specifically, a cross sectional view at D-D of FIG. 18.

FIG. 20 is a horizontal cross sectional view of a photocatalytic device after being attached to the attachment unit according to Fourth Embodiment, specifically, a cross sectional view at E-E of FIG. 18.

FIG. 21 is a front perspective view of the attachment unit according to Fourth Embodiment.

FIG. 22 is a rear perspective view of the attachment unit according to Fourth Embodiment.

FIG. 23 is a rear view of the attachment unit according to Fourth Embodiment.

FIG. 24 is a vertical cross sectional view of the attachment unit according to Fourth Embodiment, specifically, a cross sectional view at F-F of FIG. 23.

FIG. 25 is a rear perspective view of a photocatalytic device according to Fourth Embodiment.

FIG. 26 is a rear view of the photocatalytic device according to Fourth Embodiment.

FIG. 27 is a vertical cross sectional view of the photocatalytic device according to Fourth Embodiment, specifically, a cross sectional view at G-G of FIG. 26.

FIG. 28 is a vertical cross sectional view of a photocatalytic device and an attachment unit, showing the photocatalytic device according to Fourth Embodiment being attached to the attachment unit.

FIG. 29 is a schematic diagram showing a slide configuration of a magnet according to Fifth Embodiment.

DESCRIPTION OF THE PREFERRED EMBODIMENTS

The following describes embodiments of the present invention with reference to the accompanying drawings. In the following descriptions, like elements are given like reference numerals. Such like elements will be referred to by the same names, and have the same functions. Accordingly, detailed descriptions of such elements will not be repeated. In the following descriptions of photocatalytic device 100, including the photocatalytic unit 110 of photocatalytic device 100, the terms used to refer to directions, for example, front, back, left, right, top, and bottom, are relative to the vertically placed position of the photocatalytic device 100, as shown in FIGS. 1 and 2.

First Embodiment

External Configuration of Photocatalytic Device 100

The external configuration of a photocatalytic device 100 according to the present embodiment is described first. Referring to FIGS. 1 and 2, the photocatalytic device 100 according to the present embodiment is configured to be mountable on a wall. The photocatalytic device 100 and a cabinet 101 have a thin configuration front to back. The photocatalytic device 100 and the cabinet 101 are configured to be substantially square in shape as viewed from the front. The cabinet 101 has an inlet 102 at the bottom. The cabinet 101 has an outlet 103 at the top. A front panel 109 is attached to the front of the cabinet 101.

A depression 106 is formed in the back surface of the cabinet 101. At the left and right ends on the upper end of the depression 106 are formed attachment tabs 108 for catching an attachment unit (described later). The attachment tabs 108 and the upper end of the depression 106 form recesses for catching the attachment unit.

The bottom surface of the cabinet 101 has screw holes 107 used to screw attachment ribs formed at the bottom of the attachment unit described below.

Internal Configuration of Photocatalytic Device 100

The internal configuration of the photocatalytic device 100 according to the present embodiment is described below. Referring to FIGS. 3 to 5, the main components of the photocatalytic device 100 according to the present embodiment include a photocatalytic unit 110, a fan 120, and an LED light 140. These are included inside the cabinet 101.

The fan 120 is disposed in the vicinity of the inlet 102 at the bottom of the cabinet 101. A filter 129 is detachably provided between the fan 120 and the inlet 102. The filter 129 is provided to reduce the possibility of dust and foreign objects being drawn into the fan 120.

The fan 120 draws air from the lower front via the filter 129, and discharges air upwardly from the upper back. In the present embodiment, a light shield 1021 is provided above and behind the filter 129. The light shield 1021 is provided to prevent light from the LED light 140 from leaking through the inlet 102 while ensuring a smooth airflow from the fan 120 toward a photocatalyst sheet 112.

In the present embodiment, the fan 120 is a crossflow fan, and includes a motor 121, a rotational shaft 122, and a plurality of vanes 123.

The photocatalytic unit 110 and the LED light 140 are disposed face to face above the fan 120, or, in other words, at substantially the middle between the top and bottom of the cabinet 101. The airflow created by the fan 120 travels upward between the photocatalytic unit 110 and the LED light 140.

To describe more specifically, the photocatalytic unit 110 includes a case 111, the photocatalyst sheet 112, a plurality of vertical frames 113, and a plurality of horizontal frames 114.

By photoreaction, the photocatalyst sheet 112 decomposes the air oxygen and moisture adsorbed to its surface, and generates highly reactive superoxide anion ($O_2^-$) and OH radical (.OH). The superoxide anion ($O_2^-$) and OH radical (.OH) are able to decompose odor components and remove germs, and reduce deterioration of food by decomposing ethylene gas. Examples of the photocatalyst sheet 112 include, but are not limited to, zinc oxide (ZnO), cadmium sulfide (CdS), tungsten trioxide ($WO_3$), and titanium dioxide ($TiO_2$).

In the present embodiment, as illustrated in FIGS. 6 to 9, the photocatalytic unit 110 can be slid to the left to detach it from the cabinet 101.

To describe more specifically, as illustrated in FIGS. 10 to 12, the case 111 is configured from a left frame 111A constituting the left side, a back frame 111B constituting the whole back surface, and a right frame 111C constituting the right side. The left frame 111A has a handle 111D, enabling a user to pull out the photocatalytic unit 110 from the cabinet 101 with ease. By removing the photocatalytic unit 110, a user is able to wash the surfaces of the photocatalyst sheet 112 of the photocatalytic unit 110 with water.

The case 111 is configured so that it becomes secured in position upon being inserted all the way into the cabinet 101. Here, the case 111 is secured to such an extent that a user feels some resistance through the handle 111D when pulling out the photocatalytic unit 110 from the cabinet 101, enabling even users with a weak grip to pull out the photocatalytic unit 110. That is, a strong force is not needed to pull out the photocatalytic unit 110 from the cabinet 101.

In the photocatalytic unit 110 according to the present embodiment, the vertical frames 113 and horizontal frames 114 are provided on the front-surface side of the photocatalyst sheet 112 so that a user has a reduced possibility of touching the photocatalyst sheet 112 when washing the photocatalytic unit 110.

Specifically, in the photocatalytic unit 110 according to the present embodiment, the vertical frames 113 and horizontal frames 114 are provided away from the surface of the photocatalyst sheet 112. This makes it even less likely that a user touches the photocatalyst sheet 112. To be more specific, the vertical frames 113 is configured so that each vertical frame has standing portions 113A rising at the bottom and top of the case 111, bending portions 113B bending toward the middle between the top and bottom of the photocatalytic unit 110, and a middle portion 113C facing the photocatalyst sheet 112, parallel to the photocatalyst sheet 112. The vertical frames 113 support the horizontal frames 114 away from the photocatalyst sheet 112, and the horizontal frames 114 face the photocatalyst sheet 112, parallel to the photocatalyst sheet 112.

In the present embodiment, the photocatalytic unit 110 is configured so that, inside the cabinet 101, the number of horizontal frames 114, which are perpendicular to the airflow from the fan 120, is smaller than the number of vertical frames 113, which are parallel to the airflow from the fan 120. In this way, a resistance to the airflow from the fan 120 can be reduced while providing protection for the photocatalyst sheet 112.

Referring back to FIGS. 3 to 5, the LED light 140 includes a substrate 141 facing the photocatalyst sheet 112 of the photocatalytic unit 110 in parallel, and a plurality of main light units 142 disposed by being dispersed throughout the surface of the substrate 141.

The cabinet 101 has the outlet 103 above the photocatalytic unit 110 and the LED light 140. In the present embodiment, a plurality of light shields 1031 is provided for the outlet 103. Specifically, the light shields 1031 have a form of a dogleg as viewed in a vertical cross section. The light shields 1031 are provided so that direct light from the LED light 140 and stray light produced by reflection are prevented from leaking through the outlet 103.

Functional Configuration of Photocatalytic Device 100

The photocatalytic device 100 according to the present embodiment is described below with regard to its functional configuration. As illustrated in FIG. 13, the photocatalytic device 100 mainly includes a control unit 130 disposed anywhere in the cabinet 101, a control 170 disposed on any of the outer walls of the cabinet 101, a contact sensor 171, the LED light 140, the fan 120, and a power unit 150. The power unit 150 may be a connector or an adapter that takes power from outside, or may be a battery housed inside the cabinet 101.

Upon power being turned on via the control 170, the control unit 130 uses the power from the power unit 150 to drive the fan 120 and turn on the LED light 140. In response, the fan 120 draws air through the inlet 102, and the photocatalytic unit 110 sterilizes and deodorizes the air before it discharges through the outlet 103.

In the present embodiment, the contact sensor 171 is disposed in the vicinity of the right end of the photocatalytic unit 110 of when the photocatalytic unit 110 is inserted all the way to the right inside the cabinet 101. Accordingly, the contact sensor 171 turns on in response to insertion of the photocatalytic unit 110 all the way to the right inside the cabinet 101. The control unit 130 drives the fan 120 and turns on the LED light 140 only when the contact sensor 171 is ON. Conversely, the control unit 130 does not drive the fan 120 or turn on the LED light 140 when the contact sensor 171 is OFF or the photocatalytic unit 110 is not installed in the cabinet 101. In this way, light from the LED light 140 can be prevented from leaking through the opening 105 provided for the photocatalytic unit 110, or air does not blow out through the opening 105 when the photocatalytic unit 110 is removed from the cabinet 101.

Attachment Configuration of Photocatalytic Device 100 for Walls and Other Surfaces The photocatalytic device 100 according to the present embodiment is configured so that it can be secured to a wall via an attachment unit 160, as illustrated in FIGS. 14 and 15. For the purpose of explanation, the descriptions below are based on an example where the object to be mounted on a wall surface is a photocatalytic device. However, the technology described herein is not limited to deodorization devices, and also can be used to mount other devices on a wall surface. The term "deodorization system" also is used to refer to a combination of a deodorization device and an attachment unit.

Specifically, the attachment unit 160 according to the present embodiment is formed of a plate 161 made out of a tough material such as iron. The plate 161 has holes 163 formed one each at the upper right, upper left, bottom right, and bottom left portions of the plate 161. In the present embodiment, the attachment unit 160 is anchored to a wall or other surfaces by hammering a plaster nail 165 through each hole 163.

In substantially the middle between the left and right of the attachment unit 160, the plate 161 of the attachment unit 160 has an I-shaped raised portion, or an I-shaped depression 162, appearing raised on the back as shown in FIG. 14 or depressed on the front as shown in FIG. 15. This increases the strength of the attachment unit 160.

Referring to FIGS. 14 and 15, a level 169 is installed in substantially the middle between the top and bottom and the left and right of the depression 162. By being disposed within the depression 162, the level 169 does not bump against the back side of the cabinet 101 when the cabinet 101 of the photocatalytic device 100 is attached to the front side of the attachment unit 160.

In the present embodiment, a raised portion 168 is formed in the depression 162, and the level 169 is embedded in the raised portion 168, as shown in FIG. 15. With this configuration, the level 169 can be prevented from contacting the depression 106 on the back side of the cabinet 101 while providing high strength.

The attachment unit 160 of the foregoing configuration according to the present embodiment can be used to attach the photocatalytic device 100 to a wall, using the following procedure.

First, a user places the attachment unit 160 against a wall surface to be installed with the photocatalytic device 100. By checking the level 169, the user adjusts the attachment unit 160 horizontally. With the attachment unit 160 horizontally placed, the user hammers a plaster nail 165 through each hole 163. This secures the attachment unit 160 to the wall surface.

In order to hold the photocatalytic device 100 against the wall, the attachment tabs 108 (recesses) on the back side of the cabinet 101 are hung on the raised profiles 164 formed at the left and right ends at the top of the attachment unit 160.

Preferably, the front side of the attachment unit 160 is provided with attachment ribs 167 at the left and right ends at the bottom of the attachment unit 160. A user fixes the attachment ribs 167 to the screw holes 107 formed at the bottom end on the back side of the cabinet 101, using, for example, screws. In this way, the photocatalytic device 100 can be secured more firmly, and becomes less likely to fall off by impact, or be stolen by being removed from the wall.

In the present embodiment, the photocatalytic device 100 is configured so that the front panel 109 is larger than the cabinet 101, as viewed from the front. This configuration allows a user to attach the front panel 109 to the front of the cabinet 101 after the top left and right ends of the depression 106 on the back side of the cabinet 101 are hung on the top left and right ends of the attachment unit 160 with the front panel 109 removed, and the photocatalytic device 100 is screwed to the attachment unit 160 at the attachment ribs 167. This makes it easier to attach the cabinet 101 to the attachment unit 160.

As illustrated in FIG. 16, the front panel 109 can be secured to the cabinet 101 with the attachment tabs 109A provided at the top on the back side of the front panel 109, and the attachment tabs 109B provided at the bottom on the back side of the front panel 109, specifically, by hanging the attachment tabs 109A on the upper end of the cabinet 101, and inserting the attachment tabs 109B into the cabinet 101 at the bottom.

The attachment unit 160 is not necessarily required to be configured entirely from a plate, and may have a resin-plate configuration with the plate forming only a part of attachment unit 160.

Second Embodiment

In the foregoing embodiment, the photocatalytic unit 110 has vertical frames 113 and horizontal frames 114. However, the photocatalyst sheet 112 may be protected only with the vertical frames 113, without providing horizontal frames 114. With this configuration, a resistance to the airflow from the fan 120 can be further reduced while providing protection for the surface of the photocatalyst sheet 112.

Third Embodiment

In the foregoing embodiments, the light shields 1031 have a dogleg shape as viewed in a vertical cross section. However, because the purpose of light shields 1031 is to prevent light from the LED light 140 from leaking through the outlet 103, the shape of the light shields 1031 is not limited to a dogleg shape, and the light shields 1031 may have an arc or a straight shape as viewed from the side.

The number of light shields 1031 is not limited to three, and one or two, or four or more light shields 1031 may be provided.

In another configuration, light from the LED light 140 can be prevented from leaking through the inlet 102 by adjusting the number of vanes or the arrangement or shape of the vanes of the fan 120, instead of providing the light shield 1021.

In another configuration, light from the LED light 140 can be prevented from leaking through the outlet 103 by additionally providing a fan for the outlet 103, or by adjusting the number of vanes or the arrangement or shape of the vanes of such an additional fan, instead of providing the light shields 1031.

The outlet 103 may be formed using a dark color material, or may be coated with a dark color. In this way, reflection of light can be reduced to more effectively prevent reflected light from leaking through the outlet 103.

Fourth Embodiment

The wall attachment configuration of the photocatalytic device 100 is not limited to the ones described in the foregoing embodiments. To describe more specifically, a photocatalytic device 100 of the present embodiment is configured to be thin perpendicular to the wall surface, and long parallel to the wall surface. Specifically, the photocatalytic device 100 has a horizontally and vertically long configuration. Because of this configuration, a user does not have clear visual access to the back side of the photocatalytic device 100 when attaching the photocatalytic device 100 to the attachment unit. For example, the photocatalytic device 100 is configured to be about 0 to 20 cm perpendicular to the wall surface, about 30 cm to 100 cm horizontally, and about 30 cm to 100 cm vertically.

The photocatalytic device 100 and the attachment unit 260 according to the present embodiment therefore have a configuration that makes it easier to attach the photocatalytic device 100 to the attachment unit 260. In the present embodiment, a user attaches the photocatalytic device 100 to the attachment unit 260 after attaching the attachment unit 260 to the wall surface, as in the foregoing embodiments.

A combination of the photocatalytic device 100 and the attachment unit 260 will also be referred to as wall attachment system 1.

As illustrated in FIGS. 17 to 28, the attachment unit 260 according to the present embodiment is formed entirely of a resin plate 261. The attachment unit 260 has a plurality of vertical and horizontal reinforcement ribs 262.

As in the foregoing embodiments, the attachment unit 260 of the present embodiment is configured so that the attachment tabs 108 on the back side of the photocatalytic device 100 are hung on the top of the attachment unit 260. In this connection, the attachment unit 260 has a reinforcing metal plate 263 at an upper part of the attachment unit 260.

The attachment unit 260 according to the present embodiment has a level 269 at an upper part of the attachment unit 260.

The attachment unit 260 according to the present embodiment has a magnet 267 at an upper part on the front side of the attachment unit 260.

The photocatalytic device 100 has a metal panel 208 attached to the back surface of the photocatalytic device 100 in a position that faces the magnet 267 when the photocatalytic device 100 is attached to the attachment unit 260. The metal panel 208 is connected at one end to the back surface of the photocatalytic device 100 with attachment members 207.

In this way, the magnetic force of the magnet 267 pulls the metal panel 208 toward the magnet 267, and the metal panel 208 bends backward, and contacts the magnet 267 when the photocatalytic device 100 is placed in the correct position for installation on the attachment unit 260.

In the present embodiment, conditions such as the strength and size of the magnet 267, and the thickness of the metal panel 208 and the length from the attachment members are adjusted so that, in response to the photocatalytic device 100 being placed in the correct position for installation on the attachment unit 260, the metal panel 208 hits the magnet 267 under the magnetic force of the magnet 267, and makes a sound loud enough to be audible to a user. The metal panel 208 has a thickness of preferably about 1 mm, and a length of preferably 5 to 10 cm along the horizontal length of the photocatalytic device 100.

Specifically, as illustrated in FIG. 22, a user secures the attachment unit 260 to the wall surface at the upper right and left and the lower right and left portions of the attachment unit 260, using screws 265.

As illustrated in FIG. 28, with the photocatalytic device 100 held substantially vertically, a user moves the photocatalytic device 100 toward the front surface of the attachment unit 260, front to back. More specifically, with the top of the photocatalytic device 100 leaning more closely to the attachment unit 260 than the bottom, the user tilts and adjusts the photocatalytic device 100 to such a position or in such an orientation that the attachment portions 264 of the attachment unit 260 catch the attachment tabs 108 of the photocatalytic device 100.

In response to the photocatalytic device 100 having moved to the correct position for installation on the attachment unit 260, the magnetic force of the magnet 267 pulls the metal panel 208, enabling the user to correctly and easily adjust the position of the photocatalytic device 100 relative to the attachment unit 260.

In response to the photocatalytic device 100 being moved to the correct position for installation on the attachment unit 260, the metal panel 208 moves toward the magnet 267 under the magnetic force of the magnet 267, and makes a sound upon hitting the magnet 267. This enables the user to easily tell that the photocatalytic device 100 has been correctly positioned relative to the attachment unit 260.

In another configuration, the metal panel 208 hitting the magnet 267 under the magnetic force of the magnet 267 may produce a sound when the attachment portions 264 of the attachment unit 260 have fully caught the attachment tabs 108 of the photocatalytic device 100. In another configuration, the metal panel 208 hitting the magnet 267 under the magnetic force of the magnet 267 may produce a sound when the attachment portions 264 of the attachment unit 260 have partly caught the attachment tabs 108 of the photocatalytic device 100. In another configuration, the metal panel 208 hitting the magnet 267 under the magnetic force of the magnet 267 may produce a sound when the attachment tabs 108 of the photocatalytic device 100 are placed directly above the attachment portions 264 of the attachment unit 260.

Fifth Embodiment

In the foregoing embodiment, the metal panel 208, having resilience, is installed at the back surface of the photocatalytic device 100. However, the present invention is not limited to such a configuration, and may adopt other configurations to help move the photocatalytic device 100 to the correct position for installation on the attachment unit 260, or to make a sound when the photocatalytic device 100 has moved to the correct position for installation on the attachment unit 260.

For example, a magnet may be installed at an upper part of the back surface of the photocatalytic device 100, instead of providing the metal panel 208.

In this case, a metal panel may be installed at the front surface of the attachment unit 260 in a position that faces the magnet when the photocatalytic device 100 is attached to the attachment unit 260. The metal panel is connected at one end to the front surface of the attachment unit 260 with attachment members.

With this configuration, the metal panel bends toward the magnet (or bends forward) under the magnetic force of the magnet, and contacts the magnet or makes a contact sound in response to the photocatalytic device 100 being placed in the correct position for installation on the attachment unit 260.

In another configuration, two magnets may be provided face to face for the attachment unit 260 and the photocatalytic device 100, one at the front surface of the attachment unit 260, and one at the back surface of the photocatalytic device 100. In this case, one of the magnets or the both magnets are configured to be movable forward and backward.

With this configuration, the magnet moves under the magnetic force of the other magnet, and contacts the other magnet or makes a contact sound in response to the photocatalytic device 100 being placed in the correct position for installation on the attachment unit 260.

For example, as illustrated in FIG. 29, a magnet 273 is provided on the attachment unit 260 or on the back surface of the photocatalytic device 100 via a sliding member 272, allowing the magnet 273 to move forward and backward. The metal member is secured to the back surface of the photocatalytic device 100 or to the front surface of the attachment unit 260 in a position that faces the magnet 273. The sliding member 272 is urged in a direction away from the metal panel, using a spring 271 or the like.

With this configuration, the sliding member 272 slides toward the metal member under the magnetic force of the magnet 273, and the magnet contacts the metal or makes a contact sound in response to the photocatalytic device 100 being placed in the correct position for installation on the attachment unit 260.

Not surprisingly, the slide mechanism may be configured to slide the metal member forward and backward, or slide the metal panel and the magnet forward and backward. It is also possible to slide the both magnets, when two magnets are installed.

In another configuration, the magnet or magnets, and the metal member may rotate to achieve contact between the metal member and the magnet or between the magnets, or may rotate to make a contact sound in response to the photocatalytic device 100 being placed in the correct position for installation on the attachment unit 260.

Review

The foregoing embodiments provide a photocatalytic device that includes:
a cabinet;
a photocatalytic unit disposed inside the cabinet and including a photocatalyst;
a light configured to provide light to the photocatalyst; and
a fan configured to send airflow to a surface of the photocatalyst.

The photocatalytic unit is configured to be detachable from the cabinet.

Preferably, the photocatalytic unit is configured to be detachable from the cabinet by being slidable parallel to the photocatalyst and perpendicular to the airflow from the fan.

Preferably, the photocatalytic unit includes a protecting member disposed on a front-surface side of the photocatalyst and facing the photocatalyst.

Preferably, the protecting member includes a plurality of frames parallel to the airflow from the fan.

Preferably, the protecting member includes a plurality of frames parallel to the airflow from the fan, and a plurality of frames perpendicular to the airflow from the fan. The plurality of frames parallel to the airflow from the fan is disposed more densely than the plurality of frames perpendicular to the airflow from the fan.

Preferably, the protecting member has end portions rising from end portions of the photocatalytic unit, and a middle portion disposed parallel to the photocatalyst away from a surface of the photocatalyst.

The foregoing embodiments provide a photocatalytic unit that is detachable from a cabinet. The photocatalytic unit includes a photocatalyst, and a protecting frame disposed on a front-surface side of the photocatalyst and facing the photocatalyst.

The foregoing embodiments provide a photocatalytic device that includes:
a cabinet having an inlet and an outlet;
a photocatalytic unit disposed inside the cabinet and including a photocatalyst;
a light configured to provide light to the photocatalyst;
at least one fan configured to send airflow to a surface of the photocatalyst; and
at least one light shielding member configured to prevent light from the light from leaking out of the cabinet through at least one of the inlet and the outlet.

Preferably, said at least one light shielding member includes a plurality of light shields.

Preferably, said at least one light shielding member includes a light shield having a dogleg shape as viewed in a cross section.

Preferably, said at least one fan is disposed at one of the outlet and the inlet. Said at least one light shielding member is disposed at the other of the outlet and the inlet.

Preferably, said at least one fan is a first fan disposed at the inlet. Said at least one fan is a second fan disposed at the outlet. Said at least one light shielding member is configured so that the first fan prevents light from the light from leaking out of the cabinet through the inlet, and that the second fan prevents light from the light from leaking out of the cabinet through the outlet.

The foregoing embodiments provide an attachment unit for attaching an object to be mounted to a wall surface. The attachment unit includes an anchoring portion for securing the attachment unit to a wall surface, a supporting portion for supporting the object to be mounted, and a level.

Preferably, the attachment unit is raised or depressed for reinforcement. The level is provided in the depression.

Preferably, the anchoring portion of the attachment unit has a plurality of holes for plaster nails, and the holes are each surrounded by a depression.

The foregoing embodiments provide a deodorization system that includes an attachment unit, and a deodorization device as an object to be mounted. The deodorization device is attached to a wall surface by hanging an upper back portion of the deodorization device on a supporting portion at both ends of an upper end of the attachment unit.

Preferably, the deodorization device is screwed to the bottom of the attachment unit at the bottom.

Preferably, the deodorization device includes a front panel that is configured to be installed from the front after the deodorization device is attached to the attachment unit.

The foregoing embodiments provide a wall attachment system that includes an object to be mounted, and an attachment unit for attaching the object to be mounted to a wall surface. The object to be mounted has a back surface installed with a metal. The attachment unit has a front surface installed with a magnet. The wall attachment system is configured so that the metal and the magnet contact each other in response to the object to be mounted being set in position for installation on the attachment unit.

The foregoing embodiments provide a wall attachment system that includes an object to be mounted, and an attachment unit for attaching the object to be mounted to a wall surface. The object to be mounted has a back surface installed with a magnet. The attachment unit has a front surface installed with a metal. The wall attachment system is configured so that the metal and the magnet contact each other in response to the object to be mounted being set in position for installation on the attachment unit.

Preferably, the metal is plate-like in shape, and is configured to contact the magnet and make a contact sound by being attracted to the magnet and bending under the magnetic force of the magnet.

Preferably, the metal or the magnet is configured to be movable face to face toward the magnet or the metal, and the metal and the magnet contact each other and make a contact sound by being attracted to each other under a magnetic force.

The foregoing embodiments provide a wall attachment system that includes an object to be mounted, and an attachment unit for attaching the object to be mounted to a wall surface. The object to be mounted has a back surface installed with a magnet. The attachment unit has a front surface installed with a magnet. The wall attachment system is configured so that the magnet of the object to be mounted and the magnet of the attachment unit contact each other in response to the object to be mounted being set in position for installation on the attachment unit.

Preferably, the magnet of the object to be mounted or the magnet of the attachment unit is configured to be movable face to face toward the other magnet, and the magnets contact each other and make a contact sound by being attracted to each other under a magnetic force.

Preferably, the attachment unit is made of resin.

Preferably, the attachment unit has a reinforcing metal frame at an upper part of the attachment unit.

Preferably, the magnet or the metal is installed at an upper part of the object to be mounted.

The embodiments disclosed herein are to be considered in all aspects only as illustrative and not restrictive. The scope of the present invention is to be determined by the scope of the appended claims, not by the foregoing descriptions, and the invention is intended to cover all modifications falling within the equivalent meaning and scope of the claims set forth below.

What is claimed is:

1. A wall attachment system comprising:
   an object to be mounted; and
   an attachment unit configured to be secured to a wall surface prior to installation of the object to be mounted so as to attach the object to be mounted to the wall surface,
   wherein the object to be mounted has a back surface installed with a metal panel,
   the attachment unit has a front surface installed with a magnet,
   the metal panel is configured so that the metal panel bends in response to force from the magnet such that the metal panel and the magnet directly contact each other in response to the object to be mounted being set in position for the installation on the attachment unit, and
   the attachment unit is smaller than the object to be mounted so that the attachment unit having the object to be mounted installed thereon is invisible when the wall attachment system is viewed from a front side thereof, the front side being opposite to a side of the wall attachment system facing the wall surface.

2. A wall attachment system comprising:
   an object to be mounted; and
   an attachment unit configured to be secured to a wall surface prior to installation of the object to be mounted so as to attach the object to be mounted to the wall surface,
   wherein the object to be mounted has a back surface installed with a magnet attached to part of the back surface,
   the attachment unit has a front surface installed with a metal panel attached to part of the front surface at a position facing the magnet installed on the part of the back surface of the object to be mounted,
   the metal panel is configured so that the metal panel bends in response to force from the magnet such that the metal panel and the magnet directly contact each other in response to the object to be mounted being set in position for the installation on the attachment unit, and
   the attachment unit is smaller than the object to be mounted so that the attachment unit having the object to be mounted installed thereon is invisible when the wall attachment system is viewed from a front side thereof, the front side being opposite to a side of the wall attachment system facing the wall surface.

3. The wall attachment system according to claim 1, wherein the metal panel is in a plate shape, and is configured to contact the magnet and make a contact sound by being attracted to the magnet and bended by magnetic force of the magnet.

4. The wall attachment system according to claim 1, wherein
the metal panel and the magnet contact each other and make a contact sound by being attracted to each other by magnetic force of the magnet.

5. A wall attachment system comprising:
an object to be mounted; and
an attachment unit configured to be secured to a wall surface prior to installation of the object to be mounted so as to attach the object to be mounted to the wall surface,
wherein the object to be mounted has a back surface installed with a first magnet,
the attachment unit has a front surface installed with a second magnet,
the object to be mounted and the wall attachment system are configured so that at least one magnet selected from the group consisting of the first magnet and the second magnet bends in response to magnetic force such that the first magnet of the object to be mounted and the second magnet of the attachment unit directly contact each other in response to the object to be mounted being set in position for the installation on the attachment unit, and
the attachment unit is smaller than the object to be mounted so that the attachment unit having the object to be mounted thereon is invisible when the wall attachment system is viewed from a front side thereof, the front side being opposite to a side of the wall attachment system facing the wall surface.

6. The wall attachment system according to claim 5, wherein the first magnet and the second magnet contact each other and make a contact sound by being attracted to each other by magnetic force thereof.

7. The wall attachment system according to claim 1, wherein the attachment unit includes a resin.

8. The wall attachment system according to claim 1, wherein the attachment unit has a reinforcing metal frame at an upper part of the attachment unit.

9. The wall attachment system according to claim 1, wherein the metal panel is installed at an upper part of the object to be mounted.

10. The wall attachment system according to claim 2, wherein the magnet is installed at an upper part of the object to be mounted.

11. The wall attachment system according to claim 5, wherein the first magnet is installed at an upper part of the object to be mounted.

12. The wall attachment system according to claim 1, wherein the metal panel is attached to part of the back surface of the object to be mounted, and
the magnet is attached to part of the front surface at a position facing the metal panel installed on the part of the back surface of the object to be mounted.

13. The wall attachment system according to claim 5, wherein the first magnet is attached to part of the back surface of the object to be mounted, and
the second magnet is attached to part of the front surface at a position facing the first magnet installed on the part of the back surface of the object to be mounted.

* * * * *